(12) United States Patent
Krig et al.

(10) Patent No.: US 8,306,619 B2
(45) Date of Patent: *Nov. 6, 2012

(54) APPARATUS AND METHOD FOR TREATING VENTRICULAR TACHYARRHYTHMIAS

(75) Inventors: David B. Krig, Minneapolis, MN (US); James O. Gilkerson, Stillwater, MN (US); Robert D. Dreher, Roseville, MN (US); Jan D. Wald, Edina, MN (US); William J. Linder, Golden Valley, MN (US); William L. Zimmer, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/246,400

(22) Filed: Sep. 27, 2011

(65) Prior Publication Data

US 2012/0016433 A1  Jan. 19, 2012

Related U.S. Application Data

(60) Continuation of application No. 09/376,245, filed on Aug. 18, 1999, now Pat. No. 6,151,524, and a division of application No. 12/386,567, filed on Apr. 20, 2009, now Pat. No. 8,046,068, which is a division of application No. 11/073,818, filed on Mar. 7, 2005, now Pat. No. 7,522,956, which is a continuation of application No. 10/008,367, filed on Nov. 13, 2001, now Pat. No. 7,113,824, which is a continuation of application No. 09/686,585, filed on Oct. 11, 2000, now Pat. No. 6,317,632, which is a continuation of application No. 08/947,256, filed on Oct. 8, 1997, now Pat. No. 5,978,707.

(60) Provisional application No. 60/045,212, filed on Apr. 30, 1997.

(51) Int. Cl.
*A61N 1/362* (2006.01)
(52) U.S. Cl. .......................................................... 607/14
(58) Field of Classification Search .................. 607/4, 5, 607/14
See application file for complete search history.

(56) References Cited

U.S. PATENT DOCUMENTS 4,208,008 A    6/1980    Smith
(Continued)

FOREIGN PATENT DOCUMENTS

EP          253505          1/1988
(Continued)

OTHER PUBLICATIONS

"U.S. Appl. No. 08/947,256, Non-Final Office Action mailed Nov. 30, 1998", 12 pgs.
(Continued)

*Primary Examiner* — George Evanisko
(74) *Attorney, Agent, or Firm* — Schwegman Lundberg & Woessner, P.A.

(57) ABSTRACT

A system and method for selectively treating a ventricular tachycardia based on sensed atrial and ventricular intervals from the patient's heart. A detection window of the ten most recent atrial and ventricular intervals are analyzed for the occurrence of either tachycardia or fibrillation. When a majority of the sensed intervals are satisfied, the apparatus starts a duration time interval. Ventricular intervals and atrial intervals are compare, ventricular interval greater than the atrial interval by a bias factor the system delivers tachycardia therapy to the heart. Alternatively, the method withholds tachycardia therapy to the heart when the atrial rate is classified as atrial fibrillation and the ventricular response is unstable.

20 Claims, 8 Drawing Sheets

U.S. PATENT DOCUMENTS

| | | |
|---|---|---|
| 4,336,810 A | 6/1982 | Anderson et al. |
| 4,432,360 A | 2/1984 | Mumford et al. |
| 4,531,527 A | 7/1985 | Reinhold, Jr. et al. |
| 4,583,553 A | 4/1986 | Shah et al. |
| 4,721,114 A | 1/1988 | DuFault et al. |
| 4,802,491 A | 2/1989 | Cohen et al. |
| 4,838,278 A | 6/1989 | Wang et al. |
| 4,884,345 A | 12/1989 | Long |
| 4,924,875 A | 5/1990 | Chamoun |
| 4,940,054 A | 7/1990 | Grevis et al. |
| 5,000,189 A | 3/1991 | Throne et al. |
| 5,002,052 A | 3/1991 | Haluska |
| 5,012,814 A | 5/1991 | Mills et al. |
| 5,014,284 A | 5/1991 | Langer et al. |
| 5,014,698 A | 5/1991 | Cohen |
| 5,020,540 A | 6/1991 | Cahmoun |
| 5,042,480 A | 8/1991 | Hedin et al. |
| 5,107,850 A | 4/1992 | Olive |
| 5,113,869 A | 5/1992 | Nappholz et al. |
| 5,139,028 A | 8/1992 | Steinhaus et al. |
| 5,156,148 A | 10/1992 | Cohen |
| 5,161,527 A | 11/1992 | Nappholz et al. |
| 5,184,614 A | 2/1993 | Collins et al. |
| 5,184,615 A | 2/1993 | Nappholz et al. |
| 5,193,535 A | 3/1993 | Bardy et al. |
| 5,193,550 A | 3/1993 | Duffin |
| 5,215,098 A | 6/1993 | Steinhaus et al. |
| 5,217,021 A | 6/1993 | Steinhaus et al. |
| 5,240,009 A | 8/1993 | Williams |
| 5,247,021 A | 9/1993 | Fujisawa et al. |
| 5,255,186 A | 10/1993 | Steinhaus et al. |
| 5,271,411 A | 12/1993 | Ripley et al. |
| 5,273,049 A | 12/1993 | Steinhaus et al. |
| 5,275,621 A | 1/1994 | Mehra |
| 5,280,792 A | 1/1994 | Leong et al. |
| 5,292,348 A | 3/1994 | Saumarez et al. |
| 5,311,874 A | 5/1994 | Baumann et al. |
| 5,312,445 A | 5/1994 | Nappholz et al. |
| 5,313,953 A | 5/1994 | Yomtov et al. |
| 5,350,406 A | 9/1994 | Nitzsche et al. |
| 5,360,436 A | 11/1994 | Alt et al. |
| 5,360,437 A | 11/1994 | Thompson |
| 5,366,487 A | 11/1994 | Adams et al. |
| 5,379,776 A | 1/1995 | Murphy et al. |
| 5,388,578 A | 2/1995 | Yomtov et al. |
| 5,395,373 A | 3/1995 | Ayers |
| 5,400,795 A | 3/1995 | Murphy et al. |
| 5,411,031 A | 5/1995 | Yomtov |
| 5,437,285 A | 8/1995 | Verrier et al. |
| 5,447,519 A | 9/1995 | Peterson |
| 5,447,524 A | 9/1995 | Alt |
| 5,456,261 A | 10/1995 | Luczyk |
| 5,458,623 A | 10/1995 | Lu et al. |
| 5,474,574 A | 12/1995 | Payne et al. |
| 5,503,159 A | 4/1996 | Burton |
| 5,509,927 A | 4/1996 | Epstein et al. |
| 5,520,191 A | 5/1996 | Karlsson et al. |
| 5,522,850 A | 6/1996 | Yomtov et al. |
| 5,523,942 A | 6/1996 | Tyler et al. |
| 5,542,430 A | 8/1996 | Farrugia et al. |
| 5,545,182 A | 8/1996 | Stotts et al. |
| 5,549,654 A | 8/1996 | Powell |
| 5,554,174 A | 9/1996 | Causey, III |
| 5,560,370 A | 10/1996 | Verrier et al. |
| 5,591,215 A | 1/1997 | Greenhut et al. |
| 5,605,159 A | 2/1997 | Smith et al. |
| 5,607,460 A | 3/1997 | Kroll et al. |
| 5,609,158 A | 3/1997 | Chan |
| 5,613,495 A | 3/1997 | Mills et al. |
| 5,620,471 A | 4/1997 | Duncan |
| 5,628,326 A | 5/1997 | Arand et al. |
| 5,634,468 A | 6/1997 | Platt et al. |
| 5,645,070 A | 7/1997 | Turcott |
| 5,674,250 A | 10/1997 | de Coriolis et al. |
| 5,674,251 A | 10/1997 | Combs et al. |
| 5,676,153 A | 10/1997 | Smith et al. |
| 5,682,900 A | 11/1997 | Arand et al. |
| 5,683,425 A | 11/1997 | Hauptmann |
| 5,683,429 A | 11/1997 | Mehra |
| 5,687,737 A | 11/1997 | Branham et al. |
| 5,704,365 A | 1/1998 | Albrecht et al. |
| 5,712,801 A | 1/1998 | Turcott |
| 5,713,367 A | 2/1998 | Arnold et al. |
| 5,716,382 A | 2/1998 | Snell |
| 5,716,384 A | 2/1998 | Snell |
| 5,718,235 A | 2/1998 | Golosarsky et al. |
| 5,724,985 A | 3/1998 | Snell et al. |
| 5,725,559 A | 3/1998 | Alt et al. |
| 5,738,105 A | 4/1998 | Kroll |
| 5,741,304 A | 4/1998 | Patwardhan et al. |
| 5,749,901 A | 5/1998 | Bush et al. |
| 5,755,736 A | 5/1998 | Gillberg et al. |
| 5,759,196 A | 6/1998 | Hess et al. |
| 5,766,225 A | 6/1998 | Kramm |
| 5,772,604 A | 6/1998 | Langberg et al. |
| 5,779,645 A | 7/1998 | Olson et al. |
| 5,792,065 A | 8/1998 | Xue et al. |
| 5,795,303 A | 8/1998 | Swanson et al. |
| 5,797,399 A | 8/1998 | Morris et al. |
| 5,797,849 A | 8/1998 | Vesely et al. |
| 5,814,081 A | 9/1998 | Ayers et al. |
| 5,817,133 A | 10/1998 | Houben |
| 5,819,741 A | 10/1998 | Karlsson et al. |
| 5,827,197 A | 10/1998 | Bocek et al. |
| 5,840,079 A | 11/1998 | Warman et al. |
| 5,842,997 A | 12/1998 | Verrier et al. |
| 5,848,972 A | 12/1998 | Triedman et al. |
| 5,853,426 A | 12/1998 | Shieh |
| 5,857,977 A | 1/1999 | Caswell et al. |
| 5,865,838 A | 2/1999 | Obel et al. |
| 5,868,680 A | 2/1999 | Steiner et al. |
| 5,873,897 A | 2/1999 | Armstrong et al. |
| 5,891,170 A | 4/1999 | Nitzsche et al. |
| 5,935,082 A | 8/1999 | Albrecht et al. |
| 5,954,661 A | 9/1999 | Greenspon et al. |
| 5,968,079 A | 10/1999 | Warman et al. |
| 5,978,707 A * | 11/1999 | Krig et al. ............ 607/14 |
| 5,987,354 A | 11/1999 | Cooper et al. |
| 5,991,657 A | 11/1999 | Kim |
| 5,991,662 A | 11/1999 | Kim et al. |
| 5,999,850 A | 12/1999 | Dawson et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,081,746 A | 6/2000 | Pendekanti et al. |
| RE36,765 E | 7/2000 | Mehra |
| 6,085,116 A | 7/2000 | Pendekanti et al. |
| 6,088,618 A | 7/2000 | Kerver |
| 6,091,988 A | 7/2000 | Warman et al. |
| 6,108,578 A | 8/2000 | Bardy et al. |
| 6,151,524 A * | 11/2000 | Krig et al. ............ 607/14 |
| 6,178,350 B1 | 1/2001 | Olson et al. |
| 6,179,865 B1 | 1/2001 | Hsu et al. |
| 6,192,273 B1 | 2/2001 | Igel et al. |
| 6,223,078 B1 | 4/2001 | Marcovecchio |
| 6,230,055 B1 | 5/2001 | Sun et al. |
| 6,240,317 B1 | 5/2001 | Villaseca et al. |
| 6,249,699 B1 | 6/2001 | Kim |
| 6,256,534 B1 | 7/2001 | Dahl |
| 6,266,554 B1 | 7/2001 | Hsu et al. |
| 6,272,380 B1 | 8/2001 | Warman et al. |
| 6,275,732 B1 | 8/2001 | Hsu et al. |
| 6,289,248 B1 | 9/2001 | Conley et al. |
| 6,308,095 B1 | 10/2001 | Hsu et al. |
| 6,312,388 B1 | 11/2001 | Marcovecchio et al. |
| 6,317,632 B1 * | 11/2001 | Krig et al. ............ 607/14 |
| 6,334,071 B1 | 12/2001 | Lu |
| 6,434,417 B1 | 8/2002 | Lovett |
| 6,449,503 B1 | 9/2002 | Hsu |
| 6,456,871 B1 | 9/2002 | Hsu et al. |
| 6,493,579 B1 | 12/2002 | Gilkerson et al. |
| 6,512,940 B1 | 1/2003 | Brabec et al. |
| 6,522,917 B1 | 2/2003 | Hsu et al. |
| 6,526,313 B2 | 2/2003 | Sweeney et al. |
| 6,658,286 B2 | 12/2003 | Seim |
| 6,671,548 B1 | 12/2003 | Mouchawar et al. |

| | | | |
|---|---|---|---|
| 7,062,326 | B2 | 6/2006 | Huvelle et al. |
| 7,101,339 | B2 | 9/2006 | Daum et al. |
| 7,113,824 | B2 * | 9/2006 | Krig et al. .................. 607/14 |
| 7,212,849 | B2 | 5/2007 | Zhang et al. |
| 7,522,956 | B2 | 4/2009 | Krig et al. |
| 7,840,265 | B2 | 11/2010 | Perschbacher et al. |
| 2002/0049474 | A1 | 4/2002 | Marcovecchio et al. |
| 2002/0065539 | A1 | 5/2002 | Von Arx et al. |
| 2002/0107552 | A1 | 8/2002 | Krig et al. |
| 2002/0123768 | A1 | 9/2002 | Gilkerson |
| 2002/0147407 | A1 | 10/2002 | Seim |
| 2002/0198461 | A1 | 12/2002 | Hsu et al. |
| 2003/0060849 | A1 | 3/2003 | Hsu |
| 2003/0109792 | A1 | 6/2003 | Hsu et al. |
| 2003/0120316 | A1 | 6/2003 | Spinelli et al. |
| 2004/0015090 | A1 | 1/2004 | Sweeney et al. |
| 2004/0093035 | A1 | 5/2004 | Schwartz et al. |
| 2004/0102908 | A1 | 5/2004 | Larson et al. |
| 2004/0116820 | A1 | 6/2004 | Daum et al. |
| 2005/0149125 | A1 | 7/2005 | Kim et al. |
| 2005/0149135 | A1 | 7/2005 | Krig et al. |
| 2007/0167849 | A1 | 7/2007 | Zhang et al. |
| 2009/0005826 | A1 | 1/2009 | Li |
| 2009/0157126 | A1 | 6/2009 | Perschbacher et al. |

FOREIGN PATENT DOCUMENTS

| | | |
|---|---|---|
| EP | 0360412 | 3/1990 |
| EP | 360412 | 3/1990 |
| EP | 0401962 | 12/1990 |
| EP | 0469817 A2 | 2/1992 |
| EP | 0506230 | 9/1992 |
| EP | 554208 | 8/1993 |
| EP | 597459 | 5/1994 |
| EP | 0597459 A2 | 5/1994 |
| EP | 0617980 | 10/1994 |
| EP | 0711531 | 5/1996 |
| EP | 744190 A2 | 11/1996 |
| EP | 0748638 | 12/1996 |
| EP | 0776630 | 6/1997 |
| EP | 0848965 | 6/1998 |
| EP | 919256 | 6/1999 |
| EP | 993842 | 4/2000 |
| EP | 1112756 | 7/2001 |
| WO | WO-9302746 A1 | 2/1993 |
| WO | WO-9509029 A2 | 4/1995 |
| WO | WO-9739681 A1 | 10/1997 |
| WO | WO-9739799 A1 | 10/1997 |
| WO | WO-9825669 | 6/1998 |
| WO | WO-9840010 A1 | 9/1998 |
| WO | WO-9848891 | 11/1998 |
| WO | WO-9853879 A1 | 12/1998 |
| WO | WO-9915232 | 4/1999 |
| WO | WO-0053089 | 9/2000 |
| WO | WO-0059573 | 10/2000 |
| WO | WO-0113993 | 3/2001 |
| WO | WO-03047690 | 6/2003 |

OTHER PUBLICATIONS

"U.S. Appl. No. 08/947,256, Non-Final Office Action mailed Jun. 5, 1998", 9 pgs.

"U.S. Appl. No. 08/947,256, Response filed Mar. 30, 1999 to Non-Final Office Action mailed Nov. 30, 1998", 11 pgs.

"U.S. Appl. No. 08/947,256, Response filed Oct. 5, 1998 to Non-Final Office Action mailed Jun. 5, 1998", 15 pgs.

"U.S. Appl. No. 09/376,245, Non-Final Office Action mailed Jan. 28, 2000", 7 pgs.

"U.S. Appl. No. 09/376,245, Non-Final Office Action mailed Feb. 23, 2000", 7 pgs.

"U.S. Appl. No. 09/376,245, Response filed Feb. 11, 2000 to Non-Final Office Action mailed Jan. 28, 2000", 4 pgs.

"U.S. Appl. No. 09/376,245, Response filed May 23, 2000 to Non-Final Office Action mailed Feb. 23, 2000", 6 pgs.

"U.S. Appl. No. 09/686,585, Non-Final Office Action mailed Jan. 31, 2001", 5 pgs.

"U.S. Appl. No. 09/686,585, Response filed Apr. 26, 2001 to Non-Final Office Action mailed Jan. 31, 2001", 7 pgs.

"U.S. Appl. No. 11/073,818, Non-Final Office Action mailed Aug. 20, 2008", 9 pgs.

"U.S. Appl. No. 11/073,818, Response filed Nov. 20, 2008 to Non Final Office Action mailed Aug. 20, 2008", 10 pgs.

"U.S. Appl. No. 12/386,567, Non Final Office Action mailed Dec. 14, 2010", 11 pgs.

"U.S. Appl. No. 12/386,567, Notice of Allowance mailed Jun. 6, 2011", 7 pgs.

"U.S. Appl. No. 12/386,567, Response filed Apr. 11, 2011 to Non Final Office Action mailed Dec. 14, 2010", 10 pgs.

"U.S. Appl. No. 12/386,567, Restriction Requirement mailed Oct. 27, 2010", 7 pgs.

"U.S. Appl. No. 12/386,587, Response filed Nov. 24, 2010 to Restriction Requirement mailed Oct. 27, 2010", 9 pgs.

"International Application Serial No. PCT/US98/07674, International Preliminary Examination Report mailed Jun. 22, 1999", 18 pgs.

"International Application Serial No. PCT/US98/07674, International Search Report mailed Jul. 21, 1998", 3 pgs.

"International Application Serial No. PCT/US98/07674, Response filed Apr. 19, 1999 to Written Opinion mailed Jan. 19, 1999", 14 pgs.

"International Application Serial No. PCT/US98/07674, Written Opinion mailed Jan. 19, 1999", 8 pgs.

Duru, Firat, et al., "The Potential for Inappropriate Ventricular Tachycardia Confirmation Using the Intracardiac Electrogram (EGM) Width Criterion", PACE, vol. 22, 1999, (Jul. 1999), 1039-1046.

Freeberg, S., "Cross-Checking of Transthoracic Impedance and Acceleration Signals", U.S. Appl. No. 10/696,729, filed Oct. 29, 2003.

Grady, T. A., et al., "Prognostic Significance of Exercise-Induced Left Bundle-Branch Block", JAMA, 279(2), (1998), 153-156.

Jenkins, J., et al., "Diagnosis of Atrial Fibrillation Using Electrogram from Chronic Leads: Evaluation of Computer Algorithm", Pacing and Clinical Electrophysiology, 11(5), (1988), 622-631.

Jung, J., et al., "Discrimination of Sinus Rhythm, Atrial Flutter, and Atrial Fibrillation Using Bipolar Endocardial Signals", Journal of Cardiovascular Electrophysiology, 9 (7), (Jul. 1998), pp. 689-695.

Kim, J., et al., "Cardiac Cycle Synchronized Sampling of Impedance Signal", Application U.S. Appl. No. 10/612,388, filed Jul. 2, 2003, 28 pgs.

Kinoshita, S., et al., "Transient Disappearance of Complete Right Bundle Branch (BBB) During Exercise", Journal of Electrocardiology, 29(3), (1996), 255-256.

Medtronic, "Marquis DR 7274 Dual Chamber Implantable Cardioverter Defibrillator", Reference Manual, (Feb. 2002), 426 pgs.

Morris, M. M., et al., "Intracardiac Electrogram Transformation: Morphometric Implications for Implantable Devices", Journal of Electrocardiology, 29 Supplement, (1996), 124-129.

Schuller, H., et al., "Far Field R-Wave Sensing—an Old Problem Repeating", Pacing and Clinical Electrophysiology, 19, Part II, NASPE Abstract No. 264, (1996), p. 631.

Seim, G., et al., "Classification of Atrial Flutter and Atrial Fibrillation Using an Atrial Dispersion Index (ADI)", Guidant CRM Therapy Research Peer Review Report Revision 2.0, (Jan. 6, 1999), 27 p.

Stahmann, J. E., et al., "Implantable Devices and Methods Using Frequency-Domain Analysis of Thoracic Signal", U.S. Appl. No. 10/612,387, filed Jul. 2, 2003, 39 pgs.

Stephany, G. R., et al., "Real-Time Estimation of Magnitude-Square Coherence for Use in Implantable Devices", IEEE Computers in Cardiology, (1992), pp. 375-378.

Sweeney, R. J., et al., "Device for Monitoring Fluid Status", U.S. Appl. No. 10/909,926, filed Aug. 2, 2004, 17 pgs.

Swiryn, S., et al., "Detection of Atrial Fibrillation by Pacemakers and Antiarrhythmic Devices", Nonpharmacological Management of Atrial Fibrillation, Chapter 21, Futura Publishing Co, Inc. Armonk, NY, (1997), pp. 309-318.

Thompson, Julie, "Template Based AV/VA Interval Comparison for the Discrimination of Cardiac Arrhythmia", U.S. Appl. No. 10/844,475, filed May 12, 2004, 33 pgs.

Zhang, Y., et al., "Method and Apparatus for Arrhythmia Detection and Discrimination Using Wireless ECG", Application Serial No. (Unassigned Serial No.) filed Oct. 28, 2004, 69 pgs.

\* cited by examiner

APPARATUS AND METHOD FOR TREATING VENTRICULAR TACHYARRHYTHMIAS

CLAIM OR PRIORITY

This application is a divisional of U.S. patent application Ser. No. 12/386,567, filed on Apr. 20, 2009, now issued as U.S. Pat. No. 8,046,068 which is a divisional of U.S. patent application Ser. No. 11/073,818, filed on Mar. 7, 2005, now issued as U.S. Pat. No. 7,522,956, which is a continuation of U.S. patent application Ser. No. 10/008,367, filed on Nov. 13, 2001, now issued as U.S. Pat. No. 7,113,824, which is continuation of U.S. patent application Ser. No. 09/686,585, filed on Oct. 11, 2000, now issued as U.S. Pat. No. 6,317,632, which is a continuation of U.S. patent application Ser. No. 09/376,245, filed on Aug. 18, 1999, now issued as U.S. Pat. No. 6,151,524, which is a continuation of U.S. patent application Ser. No. 08/947,256, filed on Oct. 8, 1997, now issued as U.S. Pat. No. 5,978,707, which claims the benefit under 35 U.S.C. 119(e) of U.S. Provisional Application No. 60/045,212 filed on Apr. 30, 1997.

FIELD OF THE INVENTION

The present invention relates generally to implantable pulse generators and in particular to implantable cardioverter-defibrillators for treating ventricular tachyarrhythmias.

BACKGROUND OF THE INVENTION

Implantable cardioverter-defibrillators (ICDs) have evolved significantly since their clinical introduction by Miroski in 1980. Initial ICDs were designed to recognize ventricular fibrillation and to deliver high-energy shocks in an attempt to treat the arrhythmia. However, clinical electrophysiology research indicated that an ICD capable of recognizing and treating ventricular tachycardias as well as ventricular fibrillation was useful for prevention of arrhythmic death.

Subsequent ICD development lead to devices that were able to treat ventricular tachycardias with antitachycardia pacing and low-energy cardioversion shocks in conjunction with back-up defibrillation therapy. These ICDs monitored the heart rate and the onset of the ventricular arrhythmia from ventricular endocardial signals to determine when the heart was in need either of cardioversion to treat a ventricular tachycardia or of defibrillation to treat ventricular fibrillation. While it was successful in detecting ventricular arrhythmias, the ICDs were unable to reliably discriminate sinus tachycardia and atrial arrhythmias, particularly paroxysmal atrial fibrillation, from malignant ventricular rhythms because of the sole reliance on ventricular cardiac signals to determine the cardiac state. As a result, the ICD might deliver inappropriate therapy based on aberrant ventricular signals that have their origins in an undetected supraventricular tachyarrhythmia, leading to an uncomfortable cardioversion shock being delivered to the patient.

In an attempt to correct this problem ICDs have been designed with dual chamber sensing capabilities to detect and analyze both ventricular and atrial endocardial signals. This increase in cardiac signal input to the ICD has provided an opportunity to determine the origin and the nature of the ventricular tachyarrhythmia, and to reduce the frequency of inappropriate therapy being delivered to an implant patient. However, while the combination of antitachycardia pacing with low and high energy shock delivery as well as backup bradycardia pacing in ICDs has expanded the number of clinical situations in which the device may appropriately be employed, means of coordinating ventricular and atrial rate information in a way that results in a system that effectively and efficiently treats an implant patient is still desired.

SUMMARY OF THE INVENTION

The present invention includes a system and a method for reducing unnecessary treatment of a rapid ventricular rate caused by a conducted atrial fibrillation. The system and method treat ventricular tachycardia by first sensing and analyzing cardiac signals from both the atrial and ventricular chambers. Pathological heart rhythms are detected by determining the patient's heart rate, the atrial/ventricular relationship of the rhythm, the suddenness of onset rate of the arrhythmia, the rate stability of the rhythm, the sustained rate duration of the arrhythmia, and whether the atria are in a state of fibrillation. This information is then used to assess the origin of a rapid ventricular rate and to determine when and what type of ventricular therapy is to be delivered to the heart. By analyzing the origin of the rapid ventricular rate prior to delivering ventricular tachycardia therapy, true ventricular tachycardia can be treated quickly and when ventricular tachycardia is of atrial origin, treatment can be delayed to determine if will convert naturally.

According to one embodiment of the present invention there is provided a system including (1) electronic control circuitry within an implantable housing coupled to implantable ventricular and atrial catheters for identifying and analyzing cardiac signals in the manner described above and for providing electrical energy to the heart to affect sinus rhythm of the heart in the manner described above in response to a signal from the electronic control circuitry indicating the occurrence of an atrial arrhythmia.

The system allows the user to partition therapy into a maximum of three programmable tachycardia therapy zones. The system provides tachycardia therapy to the patient in the form of anti-tachycardia pacing pulses, low energy cardioversion shocks, or high voltage defibrillation shocks. Anti-tachycardia pacing pulses may be adapted to the individual chamber (atrium or ventricle) depolarization rates. A variety of conversion schemes including, fixed or adaptive burst, ramp, scan, and ramp/scan, may be selected. To convert rapid ventricular tachycardia (VT) and ventricular fibrillation (VF), the system provides both monophasic and biphasic, synchronous, defibrillation shocks to the patient.

DETAILED DESCRIPTION

In the following Detailed Description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Figure 1:
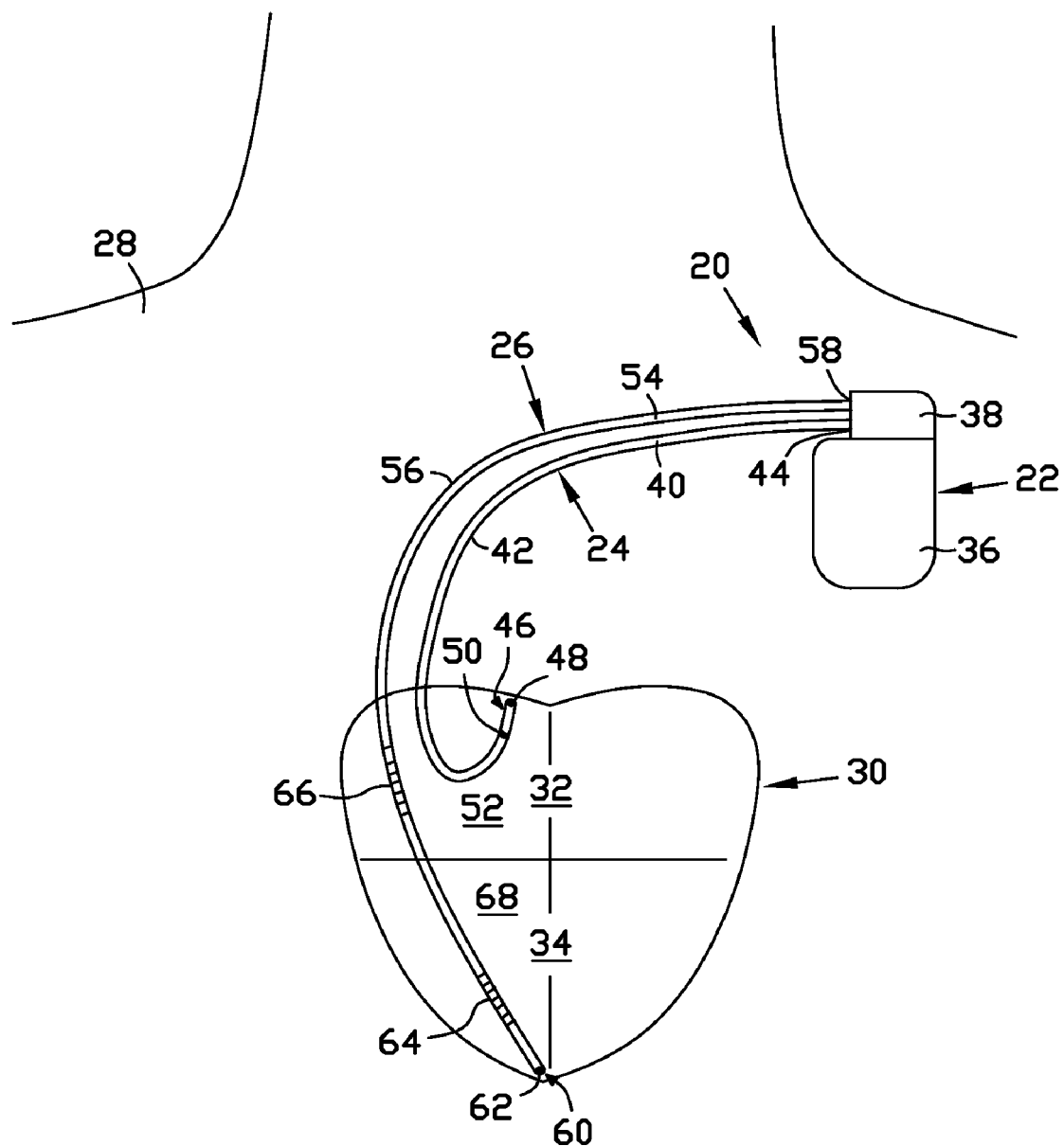
FIG. 1 is a schematic view of a cardioverter-defibrillator including a system according to the present invention that is implanted in the human body and is coupled to atrial and ventricular leads implanted in a human heart.

Referring now to FIG. 1 of the drawings, there is shown a system including an implantable pulse generator 22 physically and electrically coupled to an atrial catheter 24 and a ventricle catheter 26, which system 20 may be used in practicing the method according to the present invention. The system 20 is implanted in a human body 28 with portions of the atrial and ventricular catheters 24 and 26 inserted into a heart 30 to detect and analyze electric cardiac signals produced by both the atria 32 and the ventricles 34 of the heart 30 and to provide electrical energy to the heart 30 under certain predetermined conditions to treat ventricular tachycardias and ventricular fibrillation of the heart 30.

Figure 2:
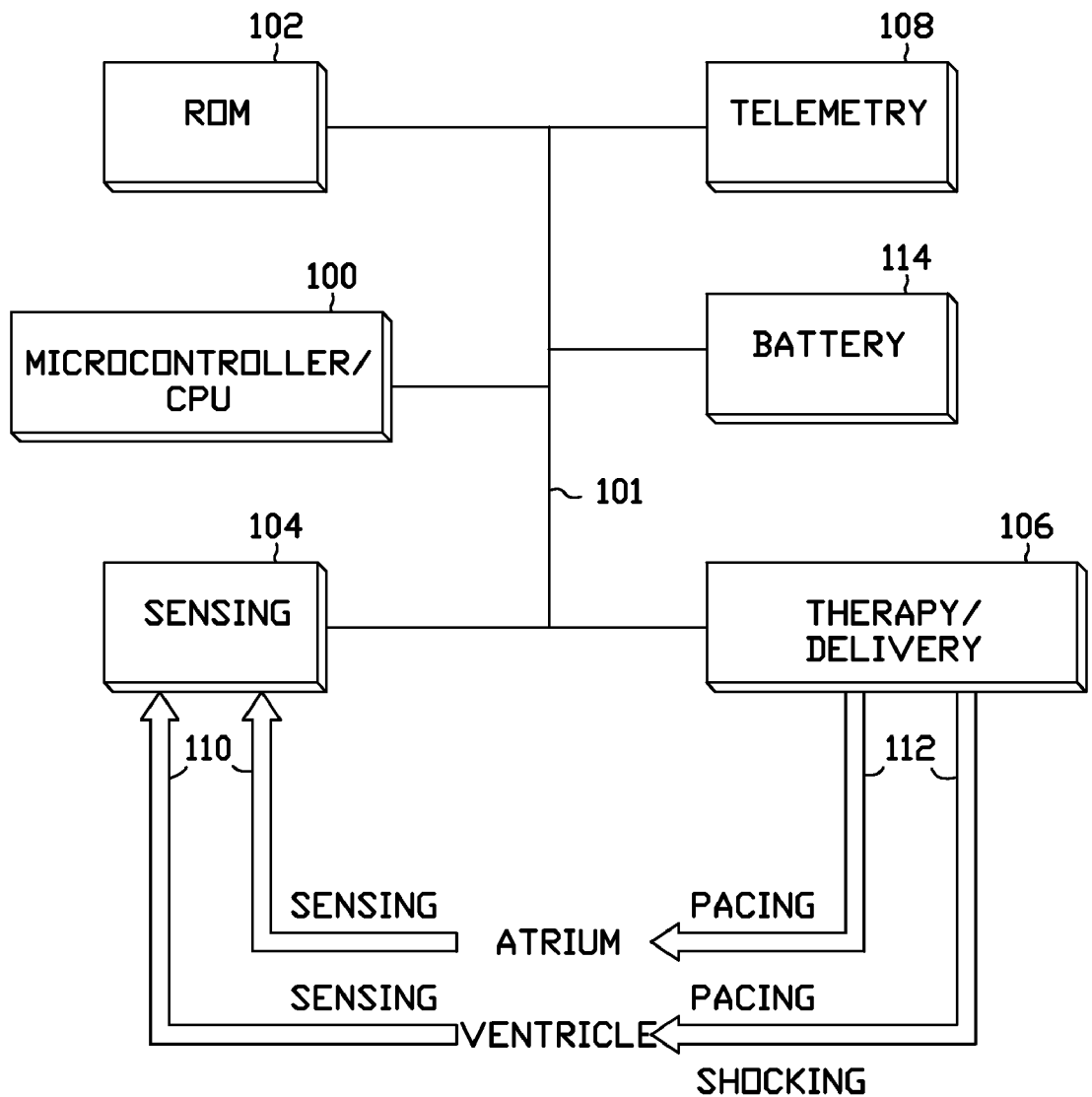
FIG. 2 is a block diagram of electronic control circuitry included in a system according to the present invention.

A schematic of the pulsed generator 22 electronics is shown in FIG. 2. The implantable pulse generator 22 comprises an implantable housing 36 which contains a microcontroller/CPU 100, read only memory (ROM) 102, sensing hardware 104, including atrial and ventricular sense amplifiers (not shown); therapy delivery hardware 106, and telemetry hardware 108. All electronic components of the pulse generator 22 are interconnected by way of a bus connection 101. The method of the system 20 is implemented in an algorithm as firmware within the ROM 102 and is executed by the microcontroller/CPU 100. The sensing hardware 104 is also connected to the microcontroller/CPU 100, and contains a plurality of electrical connections 110 coupled to the atrial and ventricular sense amplifiers. The output of the sense amplifiers is connected to the microcontroller/CPU 100, so that the atrial 32 and the ventricle 34 cardiac signals received through the sensing hardware 104 are analyzed by the algorithm within the microcontroller/CPU 100.

The microcontroller/CPU 100 is also coupled to the therapy delivery hardware 106, which controls the delivery of electrical energy to the heart 30 through a plurality of electrical output connections 112 to affect the sinus rhythm of the heart 30 under certain combinations of atrial 32 and ventricular 34 conditions. Power to the implantable pulse generator 22 is supplied by an electrochemical battery 114 that is housed within the implantable pulse generator 22. The implantable pulse generator 22 is interrogated and programmed via bi-directional radio frequency telemetry through the telemetry hardware 108 with an external programmer.

Referring again to FIG. 1, a connector block 38 is mounted on the implantable pulse generator 22. The connector block 38 has two connector ports to physically and electrically connect the atrial catheter 24 and the ventricular catheter to the sensing hardware 104 and the therapy delivery hardware 106 of the implantable pulse generator 22. Additional connector ports can be added to the connector block 38, and configurations with three or more ports are known. Alternatively, the connector block can be provided with one connector port for physically and electrically connecting an implantable transvenous catheter to the implantable pulse generator 22.

The electrical activity in the heart 30 is sensed and therapies are delivered to the heart 30 through at least one transvenous pacing/defibrillation lead connected to the implantable pulse generator 22. Unipolar and/or bipolar pacing and sensing electrodes can be used in conjunction with the at least one transvenous pacing/defibrillation lead. In the embodiment shown in FIG. 1, bipolar leads and sensing circuits are utilized for sensing both the atrial 32 and the ventricular 34 activity. Sensing atrial activity includes the determination of atrial P-waves for the purpose of determining atrial intervals, and ventricular activity is monitored by sensing for the occurrence of ventricular R-waves for the purpose of determining ventricular intervals. Pacing therapies to the atrium 32 or ventricle 34 are delivered to the heart 30 using these same leads. The system 20 also has defibrillation electrodes which are connected to the electrical output connections 112, and serve to deliver cardioversion and defibrillation level electrical pulses to the heart 30 upon a signal from the microcontroller/CPU 100 indicating a predetermined condition within the heart 30. The housing 36 of the system 20 is an optional defibrillation electrode, where the housing 36 of the implantable pulse generator 22 is electrically connected to a cathode pole of the therapy delivery hardware 106. All defibrillation electrical pulses are delivered to the heart with at least two defibrillation electrodes, or through at least one defibrillation electrode and the housing 36 of the implantable pulse generator 22. The system 20 supports a plurality of pacing regimens, including DDD pacing.

Besides the lead configuration shown in FIG. 1, the system 20 supports several other lead configurations and types. For example it is possible to use ventricular epicardial rate sensing, atrial endocardial bipolar pace/sensing, ventricular endocardial bipolar pace/sensing, epicardial patches, and Endotak® series and ancillary leads in conjunction with the implantable pulse generator 22.

Referring now to FIG. 1, there is shown an embodiment of the system 20 of present invention where the atrial catheter 24 has an elongate body 40 having a peripheral surface 42, proximal and distal ends, 44 and 46, a first atrial electrode 48 and a second atrial electrode 50 on the peripheral surface 42. The first atrial electrode 48 and the second atrial electrode 50 receive bipolar electrical cardiac signals from the right atrium chamber 52 of the heart 30, and are attached on the peripheral surface 42 of the elongate body 40.

The first atrial electrode 48 is at or adjacent to the distal end 46 of the elongate body 40 and is either a pacing tip electrode or a semi-annular electrode partially encircling or an annular electrode encircling the peripheral surface 42 of the elongate body 40. The second electrode 50 is an annular electrode encircling or semi-annular electrode partially encircling the peripheral surface 42 of the elongate body 40. The second electrode 50 is spaced longitudinally along the peripheral surface 40 from the first atrial electrode 48 and the distal end 46 of the atrial catheter 24 such that when the atrial catheter 24 is inserted into the right atrial chamber 52 of the heart 30, the first atrial electrode 48 is in physical contact with a portion of a wall of the right atrial chamber 52 of the heart 30 and the second electrode 50 is within the right atrium chamber 52.

Electrical leads extend longitudinally within the elongate body 40 of the atrial catheter 24 from a connection end at the proximal end 44 and make connection to the first and second atrial electrodes 48 and 50. The proximal end 44 of the atrial pacing catheter 24 is releasably attached to the connector block 38 of the implantable pulse generator 22 with the contact ends of the electrical leads in electrical connection with both the sense amplifiers of the sensing hardware 104 and the therapy delivery hardware 106 such that the implantable pulse generator receives bipolar signals from and delivers bipolar pacing to the right atrium 52 of the heart 30.

The ventricular catheter 26 comprises an elongate body 54 having a peripheral surface 56, proximal and distal ends, 58 and 60, and a ventricle pacing electrode 62, a first defibrillation electrode 64, and a second defibrillation electrode 66 on the peripheral surface 56 of the elongate body 54. The ventricular pacing electrode 62 and the first defibrillation electrode 64 are adapted to receive electrical cardiac signals from the right ventricle chamber 68 of the heart 30, and are attached on the peripheral surface of the elongate body 54. The second defibrillation electrode 66 is space apart and space longitudinally on the peripheral surface 56 of the ventricular catheter 26 to afford positioning the ventricular catheter 26 in the heart 30 with the ventricular pacing electrode 62 in the apex of the right ventricle 68, the first defibrillation electrode 64 within the right ventricle chamber of the heart, and the second defibrillation electrode 66 within the right atrium chamber 52 or a major vein leading to right atrium.

Electrical leads extend longitudinally within the elongate body 54 of the ventricular catheter 26 from a connection end at the proximal end 58 to make connection with the ventricular pacing electrode 62, the first defibrillation electrode 64, and the second defibrillation electrode 66. The proximal end 58 of the ventricular catheter 26 is releasably attached to the connector block 38 of the implantable pulse generator 22 with the contact ends of the electrical leads in electrical connection with both the sense amplifiers of the sensing hardware 104 and the therapy delivery hardware 106 such that the implantable pulse generator 22 receives either unipolar or bipolar signals from and can deliver unipolar or bipolar pacing to the right ventricle 68 and defibrillation electrical pulses to the ventricles 34 of the heart 30.

The atrial catheter 24 and the ventricular catheter 26 are releasably attached to and are separated from the implantable pulse generator 22 to facilitate inserting the atrial catheter 24 into the heart 30. The atrial and ventricular catheters, 24 and 26, are inserted into the heart 30 transvenously through a cephalic or subclavian vein to position the distal end 46 of the atrial catheter 24 in the right atrium chamber 52 and the distal end 60 of the ventricular catheter 26 in the apex of the right ventricular chamber 68. The proximal end 44 of the atrial catheter 24 and the proximal end of the ventricle catheter 26 are then attached to the implantable pulse generator 22. The proximal end 44 of the atrial catheter 24 and the proximal end 58 of the ventricular catheter 26 are adapted to seal together with the connector ports of the implantable pulse generator 22 to thereby engage the contact ends of the atrial catheter 24 and the ventricular catheter 26 with the plurality of electrical connections 110 and the therapy delivery hardware 106 of the implantable pulse generator 22. The implantable pulse generator 22 of the system 20 is then positioned subcutaneously within the body 26.

Figure 3:
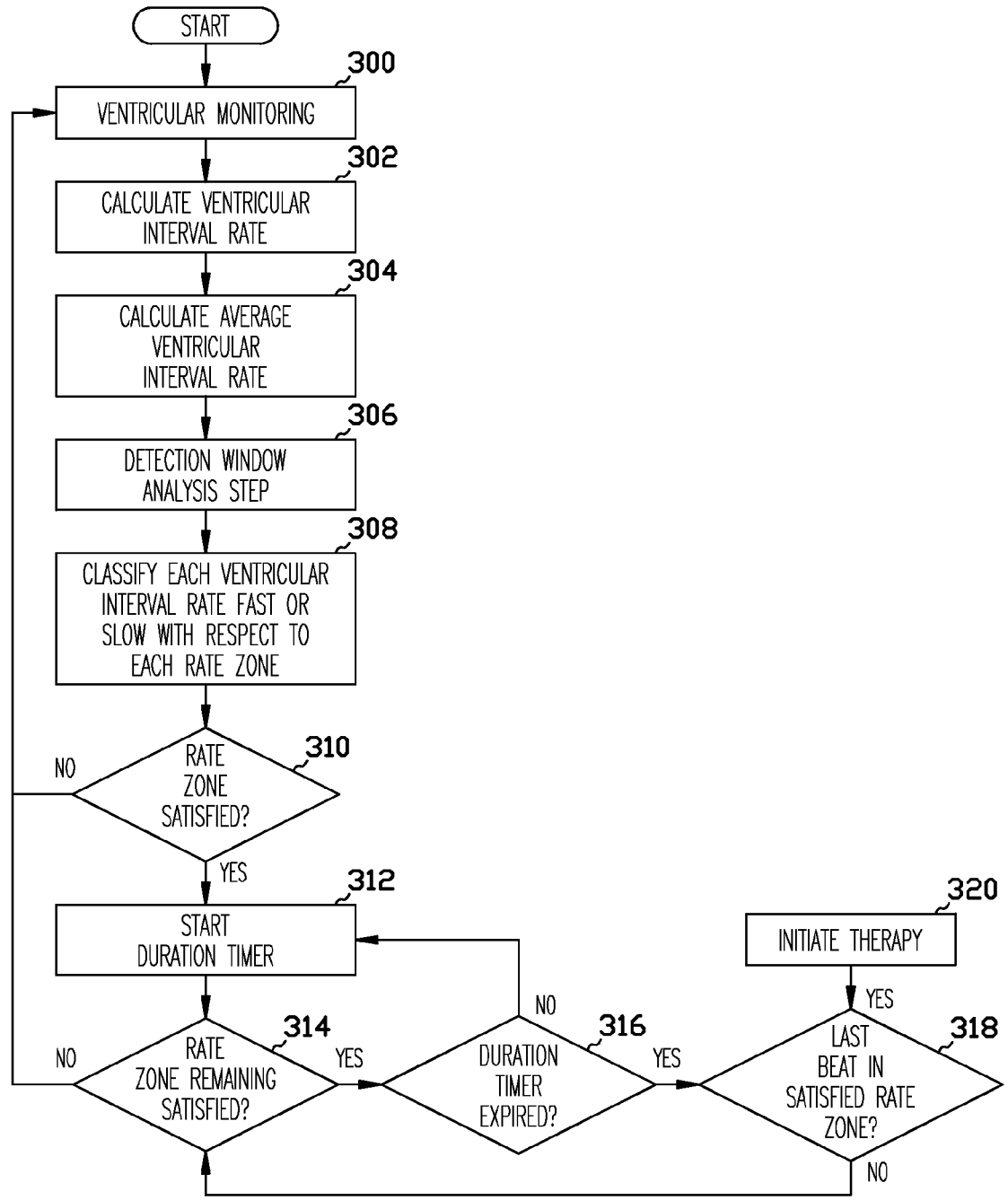
FIG. 3 is a flow diagram of a first portion of the manner in which the electronic circuitry included in the system operates according to the present invention.

Referring now to FIG. 3, there is shown a flow diagram of a first portion of the manner in which the electronic circuitry of the system 20 operate according to the present invention. Detection decisions by the system 20 are based on detected cardiac cycle lengths. Initially, the system 20 monitors and analyzes sensed ventricular events within the heart 30 during a ventricular monitoring step 300. During the ventricular monitoring step 300, the system senses the occurrence of ventricular R-waves, from which a ventricular interval rate 302 (i.e., R-R wave time interval) is calculated. The system 20 then calculates an average ventricular rate from the sensed ventricular interval rate 304.

The system 20 can be programmed to define one, two, or three rate zones that are above a defined upper limit for normal ventricular interval rates. A rate zone is a range of ventricular interval rates which is defined between a lower rate threshold, and a lower rate threshold of the next faster rate zone (if any) programmed in the system 20. For each rate zone, the lower rate threshold is a programmable value in beats per minute (bpm) and is the value to which the system 20 compares each sensed ventricular interval rate to determine the zone in which that ventricular interval rate belongs. Rate zones can be defined for slow tachycardia (VT-1), fast ventricular tachycardia (VT), and ventricular fibrillation (VF). When only one rate zone is programmed, the system only monitors for the VF rate zone; when two rate zones are programmed the system monitors the VF and the VT rate zones; and when three rate zones are programmed the system monitors the VF, VT, and the VT-1 rate zones.

The lower rate threshold for a one-zone configuration, (i.e., only the VF rate zone is programmed) can be a programmable value between 130 to 250 bpm. For a two- or three-zone configuration the lower rate threshold for the VT rate zone can be programmable between 110-210 bpm and for the VT-1 rate zone the lower rate threshold can be programmable between 90-200 bpm.

To determine if an individual ventricular interval rate falls into a programmed rate zone, the system 20 detects the intervals between a series (e.g., 4-16, 6-14, or 8-12) of the most recent consecutive ventricular R-waves. Detecting the interval between 10 of the most recent consecutive ventricular R-waves is considered to be a good sampling. This sampling is called a detection window, with a new detection window occurring with each consecutive ventricular R-wave. The system assesses the ventricular interval in relation to one of the rate zones. The use of detection windows helps to differentiate and classify ventricular tachyarrhythmias into a rate zone, and helps to ensure that the correct ventricular therapy is delivered to the patient.

As each new ventricular interval rate is measured in the ventricular monitoring step 300, it is compared to each rate zone's lower rate threshold in the detection window analysis step 306. Based on this comparison, the ventricular interval rate is classified 308 as being either a fast or a slow ventricular interval with respect to each of the rate zones. A slow ventricular interval for a given rate zone has a ventricular interval rate that is less than that rate zone's lower rate threshold, and a fast ventricular interval for a given rate zone has a ventricular interval rate that is equal to or greater than the rate zone's lower rate threshold. When a predetermined percentage of the ventricular interval rates within the detection window are classified as being fast ventricular intervals for a rate zone 310 (i.e., that predetermined percentage can be a value between 65-95, 70-90, or 75-85 percent of the ventricular interval rates, with 80 percent being an acceptable value) the system 20 is "satisfied" that the ventricular rate intervals for the heart are properly classified in that rate zone. Herein this condition is referred to as the detection window being satisfied 310. If the detection window is not satisfied, the system 20 returns to the ventricular monitoring step 300.

When a rate zone detection window becomes satisfied that the ventricular rate interval for the heart is properly classified in one of the VP, VT, or VT-1 rate zones, the system 20 switches to a cardiac episode condition and starts a duration time interval 312. A different duration time interval is associated with each rate zone. The duration time interval times a length of time during which the system continues to monitor and analyze the ventricular interval rates within the detection windows to ensure that the ventricular tachyarrhythmia of a satisfied rate zone is sustained, rather than transitory, before the system 20 initiates a selected treatment. The length of each duration time interval is programmed for each rate zone. For example, the duration time interval for the VF rate zone can be programmed for a duration between 1-15 seconds, the duration time interval for the VT rate zone can be programmed for a duration between 1-30 seconds, and the duration time interval for the VT-1 rate zone can be programmed for a duration of between 1-60 seconds. The duration time programmed for any lower rate zones must be equal to or greater then the duration time interval for a higher rate zone.

Once the system 20 becomes "satisfied" that the ventricular rate interval for the heart is properly classified in that rate zone, the system 20 also starts a rate zone remaining satisfied step 314, where the system 20 continues to monitor the ventricular interval rates within the shifting detection window to be sure that the ventricular rate interval for the heart remains properly classified in that rate zone. This condition is satisfied as long as at least a maintenance percentage of the ventricular interval rates in the subsequent detection windows remain classified as fast ventricular intervals within the satisfied rate zone. The maintenance percentage of the ventricular interval set is a value between 45-75, 55-65, or 55-65 percent of the ventricular interval set, where 60 percent is an acceptable value. Herein this condition is referred to as the detection window remaining satisfied.

The duration time interval continues to elapse so long as a satisfied detection window remains satisfied. The duration time interval is checked by the system 20 during each ventricular interval to determine if the duration time interval has expired 314. If at any point the system 20 detects fewer than the maintenance percentage of fast ventricular intervals, the duration time interval for that rate zone is reset to zero, and the system 20 returns to the ventricular monitoring step 300 for that particular rate zone which failed to remain satisfied.

The duration time interval for a rate zone runs independently of any other rate zone duration time interval. A hierarchy of rate zone duration times exists where a higher rate zone duration time interval takes precedence over a lower rate zone timer. Thus, if both a higher and a lower rate zone become satisfied, the lower rate zone duration time interval will continue to elapse, but will be ignored while the higher rate zones' duration time interval is elapsing. If the higher rate zone's duration time interval expires and the rate zone has remained satisfied, therapy for that higher rate zone will be initiated regardless of the state of the lower rate zone timer. If, however, the higher rate zone's detection window does not remain satisfied, then the duration time interval for the lower rate zone is no longer ignored and therapy for the lower rate zone will be initiated when its duration time interval expires, provided the lower rate zone remains satisfied and no higher rate zone window becomes satisfied. Alternatively, if a detection window is satisfied for a lower rate zone, subsequent ventricular interval rates that are classified in a higher rate zone, or rate zones, would be counted for keeping the lower rate zone satisfied and for satisfying the higher rate zone. If the higher rate zone were to become satisfied prior to the satisfied lower rate zones duration time interval expiring, the system 20 would deliver therapy only at the expiration of the higher rate zone duration time interval.

When the highest satisfied rate zone duration time interval expires and the last detected ventricular interval rate falls within that rate zone, therapy is initiated. This function is carried out in a last beat in zone detection step 316, where the system 20 ensures that the proper therapy is selected in the presence of a changing ventricular rate. If the last detected interval does not remain in the highest satisfied rate zone, the system 20 forces a delay in initiating therapy until the next ventricular interval by returning to the rate zone remaining satisfied step 312. Each subsequent interval will be analyzed until the ventricular interval rate is within the highest satisfied rate zone, or the window for the highest satisfied rate zone fails to remain satisfied. If the next interval is within the highest satisfied rate zone, therapy will be initiated 318. If it is not within the highest satisfied rate zone, the next interval is examined, and the process is repeated.

During any such delay because the next interval is not within the highest satisfied rate zone the system 20 can fail to remain satisfied if the ventricular interval rate decreases and the rate zone drops below the maintenance percentage. Also, during the delay there is the potential for a higher rate zone window to become satisfied if the ventricular interval rate were to increase. If a detection window for a higher rate zone does become satisfied, then the therapy selection is delayed until either the higher rate zone duration time interval expires or the detection window for the higher zone no longer remains satisfied. This ensures that the system 20 will provide the appropriate therapy for the highest satisfied rate zone. On the other hand, if for a satisfied rate zone, the number of ventricular intervals within or above that rate zone falls below the maintenance percentage the system 20 will then return to the ventricular monitoring step 300.

Once the last beat in zone criteria is met, the system 20 proceeds to initiate and deliver a ventricular tachycardia therapy in an initiate therapy step 318. The system 20 can be programmed to deliver two types of therapy to terminate ventricular tachycardia or fibrillation: antitachycardia pacing (ATP) and/or cardioversion/defibrillation shocks. Antitachycardia pacing schemes consist of bursts of pacing pulses that are delivered between the ventricular rate-sensing electrodes. Shocks are high-voltage truncated exponential pulses (monophasic or biphasic) delivered through the shocking leads synchronously with detected heart activity.

A ventricular tachycardia therapy is a therapy regimen delivered in a particular rate zone, and can consist of a combination of ATP and cardioverting/defibrillating shocks. Each rate zone can be independently programmed with a ventricular tachycardia therapy. Antitachycardia Pacing (ATP) is used to deliver a series of pacing pulses to the ventricle in order to interrupt pace-terminable ventricular tachycardia. ATP ventricular tachycardia therapies can be programmed as off, burst, ramp, scan, or ramp/scan in the VT and the VT-1 rate zones. For rate zones VT-1 and VT, a maximum of two ATP therapies and five cardioverting/defibrillating shocks are available to be programmed into the system 20. ATP therapy is not available in the VF rate zone of any configuration.

Five cardioverting/defibrillation shocks are programmable into the system 20. The shock strength of the first and second cardioverting or defibrillation shocks delivered in each rate zone are programmable values between 0.1-29 joules. The last three potential cardioverting/defibrillation shocks are given at the maximum shock output of 29 joules. All shocks are delivered synchronously with a sensed ventricular cardia event (R-wave) if possible to avoid accelerating a tachycardia into fibrillation. The shock therapy consists of programmable monophasic or biphasic cardioversion/defibrillation shocks. In addition, the polarity of the shocks is programmable, where a duty cycle of 60/40% for the biphasic waveform is considered to be an appropriate value. Once selected, the waveform type and polarity apply to all shocks delivered by the apparatus.

When programming therapies, the therapies within a rate zone must be ordered in ascending therapy strengths. All ATP therapies are considered to be of equal strength, but are of lower strength than any shock therapy. Whenever a shock therapy has been delivered, no further ATP therapy is allowed, since ATP therapy is of lower strength than shock therapy. The strength of the shock therapies is determined from the programmed energy. In a multiple rate zone configuration, therapies in a higher rate zone can be of lesser strength or equal to those in a lower rate zone; however, within each zone the therapies must be programmed in equal or increasing energy output.

In a VT-1 rate zone of a three-zone configuration, some or all of the shocks may be programmed off, starting with the maximum shocks first. If the maximum shocks are programmed off, then the second shock can be programmed off, and if the second shock is programmed off, then the first shock can be programmed off. If the arrhythmia persists in the VT-1 rate zone when some or all of the shocks are programmed off, no further therapy will be delivered unless the arrhythmia accelerates to a higher rate zone.

Based on initial detection criteria, the system 20 selects the first prescribed therapy in the rate zone in which the tachyarrhythmia is detected. After delivering the selected therapy, the system 20 begins redetection to determine whether the arrhythmia has been converted. If the arrhythmia is converted to a rate below the lowest programmed threshold, the system 20 continues monitoring until the cardiac episode ends. When the cardiac episode ends, the system 20 will again use initial detection criteria for a new cardiac episode. When a new cardiac episode is declared, the first prescribed therapy will be delivered again. If the arrhythmia is not converted and an arrhythmia is redetected in the same zone, the next programmed therapy in that zone is selected and delivered, followed again by redetection. If the arrhythmia persists in the same rate zone the therapy will progress in that rate zone. If an arrhythmia crosses a rate zone (accelerates or decelerates) following therapy delivery and is redetected in a higher or lower rate zone, a therapy of equal or greater strength than the previously delivered therapy is selected form the detected zone and delivered. The system 20 determines which shock to deliver prior to capacitor charging, based on the detected rate threshold. If during capacitor charging, the tachyarrhythmia accelerates or decelerates from the initially detected rate, the predetermined energy will be delivered. Redetection is performed after each therapy delivery to determine if further therapy is required.

After therapy delivery, the system 20 employs a redetection criteria to evaluate the rhythm and determine whether more therapy is appropriate. When redetection criteria are satisfied, the roles for therapy selection then determine the type of therapy to deliver. If an ATP scheme is being delivered, the system 20 monitors the cardiac rate after each burst and employs the same type of detection window described above, looking for eighty percent of the intervals to be fast intervals, and the redetection duration time interval to determine if the tachyarrhythmia has terminated. The ATP scheme will continue with the next burst in the sequence until any one of the following conditions is satisfied: Redetection has declared that therapy is successful (end-of-episode), the specified number of ATP bursts in the scheme has been delivered, the ATP time-period for the zone has expired, the detected tachyarrhythmia rate changes to a different rate zone whereby a different therapy is selected, stability analysis forces therapy to skip over ATP therapy to initiate shock therapy.

If shock therapy is being delivered, the system 20 monitors the cardiac rate after each shock and employs the same type of detection window described above, looking for eighty percent of the interval to be fast intervals, and the post-shock duration time to determine if the tachyarrhythmia has terminated. Shock therapy will continue until one of the following conditions is satisfied: redetection has declared that therapy is successful (end-of-cardiac episode), all five available shocks have been delivered for a cardiac episode, all shocks programmed in the VT-r zone have been delivered and the rate stays in the VT-1 zone. If all available shock have been delivered for a cardiac episode, no further therapy is available until the system 20 monitors a rate below the lowest rate threshold for 30 seconds and end-of-cardiac episode is declared.

Cardiac episodes can be classified as either treated or non-treated where a treated episode is one in which a satisfied detection window remains satisfied and the therapy is delivered. A non-treated episode is one in which a detection window is initially satisfied but therapy is not delivered because the detection window fails to remain satisfied during the term of the duration time interval. A cardiac episode is declared complete when either the system 20 has terminated the cardiac episode by delivering therapy or when the cardiac episode has terminated naturally. For a treated episode, an end of episode timer starts at the point that therapy is delivered. For a non-treated episode, an end-of-episode timer starts at the point that the system 20 determines that all detection windows are no longer satisfied. The end-of-cardiac episode time intervals is intended to allow the patient to stabilize before initial detection and initial therapy are used again. The episode will be declared complete if the detection windows do not become satisfied for a specified time following the last delivered therapy. For a non-treated (no therapy delivered) the elapsed time required to declare episode over (end-of-episode timer) is 10 seconds, for treated where only ATP therapy delivered it is 10 seconds, and treated where any shock therapy delivered it is 30 seconds. If any window becomes resatisfied prior to the episode time-period being reached, the end-of-cardiac episode timer is rest to zero. It will start again when either therapy is delivered or all windows are not satisfied. Once a cardiac episode has been declared complete, the system 20 will apply initial detection and therapy to subsequent tachyarrhythmias. When the cardiac episode is terminated naturally, the cardiac episode is complete when all detection windows are no longer satisfied and remain unsatisfied for the duration of an end-of-episode time-out. The end-of-episode time-out timer is started when all detection windows are no longer satisfied. An end-of-episode time-out is intended to allow the patient's heart to stabilize before allowing the programmed therapy sequence to restart at the beginning of the algorithm.

If a rate zone detection window becomes satisfied before an end-of-episode time-out is reached, the rate duration time interval associated with that window is reset and the rate zone therapy in the programmed sequence is delivered once the rate duration time interval expires. If the end-of-episode time-out is reached and a rate zone detection window has not been satisfied, the cardiac episode is terminated. When this occurs, the current rate zone therapy sequence is terminated and the detection windows are cleared. If any detection window subsequently becomes satisfied, a new cardiac episode begins, and the analysis process starts again.

At the start of a cardiac episode the system 20 senses the atrial interval rate in addition to the ventricular rate and analyzes the cardia rhythms (both ventricular and atrial) to assess (1) whether the ventricular interval rate is or is not greater than the atrial interval rate by at least a bias factor (herein referred to as "V>A+B"), (2) the presence of atrial fibrillation, (3) the onset rate of the ventricular arrhythmia (herein referred to as "Onset rate"), and (4) the stability of the ventricular arrhythmia (herein referred to as "Stability"). These assessments are made by a series of programmable detection enhancement algorithms, which provide information about the nature of the ventricular tachycardia and the physiological state of the atria during a detected ventricular arrhythmia tachycardia.

The system 20 can be programmed so that under predetermined circumstances the detection enhancement algorithms are therapy inhibitors, inhibitor overrides, or therapy accelerators of the ventricular tachycardia and ventricular fibrillation therapy. Detection enhancements are not available for use with the VF rate zone because ventricular fibrillation requires immediate treatment to save the patient's life. For a two-zone configuration, certain of the detection enhancements can be used with the VT rate zone. These include the detection enhancements of V>A+B, the presence of atrial fibrillation, Onset rate, and Stability (any of which can be used as an inhibitor (explained below) or as an accelerator (explained below); although, Stability analysis cannot be programmed as both an inhibitor and an accelerator in the same rate zone, but can be programmed as an inhibitor when other detection enhancements are programmed as inhibitors and programmed as an accelerator only when no other detection enhancements are programmed as inhibitors). Also included is the use of a sustained rate duration time-period, which will also be discussed below. For a three zone configuration the detection enhancement of Stability as an accelerator can be programmed for use with the VT rate zone, and the detection enhancements of V>A+B, the presence of atrial fibrillation, Onset rate, and Stability used as an inhibitor to delivering therapy can be programmed for use with the VT-1 rate zone. The sustained rate duration time-period can also be used with the VT-1 rate zone programming.

A detection enhancement programmed as a therapy inhibitor can cause the delivery of a satisfied rate zone therapy to be delayed or inhibited if certain enhancement criteria are not satisfied at the end of the duration time interval. For example, the Onset rate detection enhancement can be programmed to inhibit therapy if the patient's heart rate increases gradually, as could occur when the patient begins to exercise. Also, the Stability detection enhancement can be programmed to inhibit therapy delivery if the ventricular rhythm is unstable so that the system 20 will inhibit delivering ventricular therapy when the unstable ventricular rhythm has its origins in the atria, because in order for an ATP therapy to be effective, the system 20 must anticipate the occurrence of the next beat so as to break into the re-entrant loop of the ventricular tachycardia. This may not be possible if the ventricular interval varies widely from beat to beat. The atrial fibrillation threshold and corresponding ventricular tachycardia stability enhancements can be programmed to inhibit ventricular therapy if the atrial rhythm is fast and the ventricular rhythm is unstable.

A detection enhancement therapy inhibitor may, however, be overridden by the use of a sustained rate duration (SRD) time-period. The SRD time-period is a time interval that is started at the expiration of a duration time interval for a satisfied rate zone that is the lowest rate zone in a multiple rate zone configuration. The SRD time-period timer can be used in conjunction with detection enhancements and it enables the system 20 to override the detection enhancement therapy inhibitors (atrial fibrillation rate threshold, Onset rate, and/or Stability programmed to inhibit if the ventricular rate is unstable) and deliver the therapy for the satisfied rate zone if the ventricular tachycardia is sustained for the programmed SRD time-period. The SRD time-period is not used in conjunction with the Stability detection enhancement programmed as an accelerator.

As previously mentioned, the SRD time-period is programmed only in the lowest rate zone of a multiple rate zone configuration (e.g., VT for a two-zone configuration, and VT-1 for a three rate-zone configuration), and is programmed within a range of values of from 10 seconds to 60 minutes, or to be off. The SRD time-period is used only when a detection enhancement programmed as a inhibitor is programmed on. If a detection enhancement as an inhibitor is inhibiting therapy and the detection window is remaining satisfied, the SRD time-period begins at the end of the duration time interval. If the detection window continues to remain satisfied during the SRD time-period, the programmed therapy will be delivered at the end of the SRD time-period. If the rate accelerates to a higher rate zone and the duration time interval for the higher rate zone is satisfied, therapy is initiated without waiting for SRD time period to time out.

Detection enhancement can also be programmed as an inhibitor override to cause one or more therapy inhibitors to be bypassed and therapy delivered if certain criteria are satisfied. For example, the V>A+B detection enhancement can be used to override the therapy inhibitors described above if the system 20 determines that the ventricular rate is greater than the atrial rate plus a bias factor.

Detection enhancements can be programmed as therapy accelerators to cause an acceleration of a ventricular therapy sequence whereby the system 20 skips over any remaining rate zone prescription therapies in the programmed sequence for that zone, and delivers the first shock therapy. Therapy accelerators accelerate the sequence of therapy by skipping over or interrupting an ATP scheme to initiate charging for the first programmed shock (which may be low or high energy) for the rate zone. The stability detection enhancement can be programmed to accelerate delivery of shock therapy if the system 20 determines the rhythm of the ventricle is unstable.

Figure 4A:
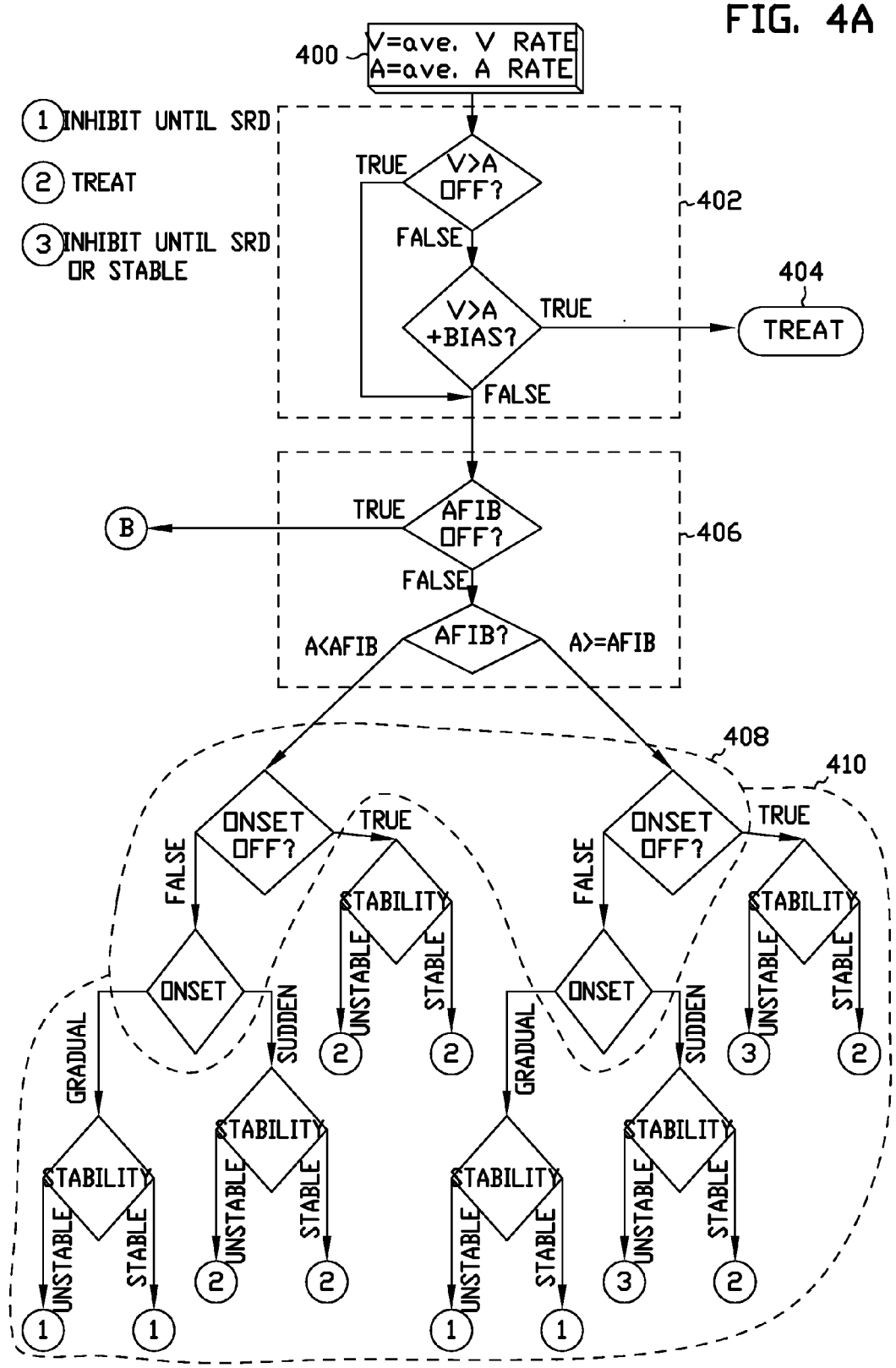
FIG. 4 is a flow diagram of a second portion of the manner in which the electronic circuitry included in the system operates according to the present invention.
Figure 4B:
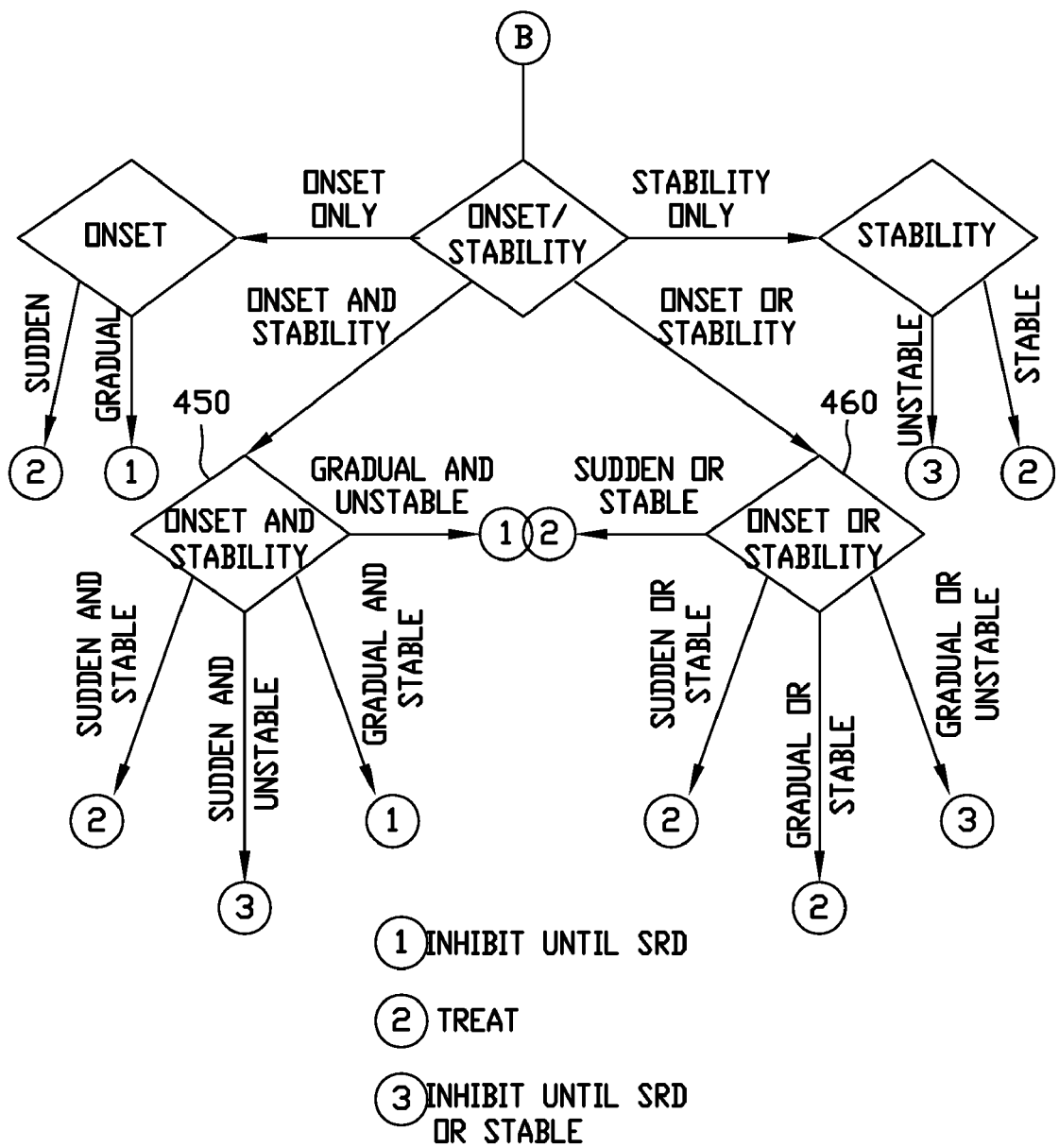

Referring to FIG. 4 there is shown a flow diagram of the detection enhancements which can be programmed and enabled within the system 20. The V>A+B, Onset rate, and Stability detection enhancements are analyzed simultaneously (if at all) following a detection window becoming satisfied. The AFib detection enhancement is analyzed following the expiration of a duration time interval for a satisfied rate zone. Therefore, FIG. 4 should not be taken to indicate any order in the analysis of atrial and/or ventricular information. Also shown in FIG. 4 are three different possible modifications to the therapy delivered to the heart based upon the results of the detection enhancements. These possible modifications to the therapy to be delivered include the result numbered number 1, which inhibits delivering therapy until the SRD time-period has expired; the result numbered number 2, which does not inhibit the delivery of therapy, and the result numbered number 3, which inhibits delivering therapy until the SRD time-period has expired or until the ventricular rhythm becomes stable as assessed by the Stability detection enhancement.

When the system 20 senses a cardiac episode (i.e., a detection window become satisfied), the system 20 has already analyzed and calculated the ventricular and the atrial interval rates in the ventricular monitoring step 300. If a V>A+B detection enhancement 402 is enabled in section 400 of FIG. 4, and a detected ventricular tachycardia is dissociated from the atrium (i.e., the ventricular tachycardia is dissociated from the atrium if the ventricular rate is greater than the atrial rate by at least a bias factor), the system 20 can make use of atrial cycle length information to bypass additional programmed detection enhancements (e.g., to bypass Onset rate and/or Stability and/or Atrial fibrillation as inhibitors) and initiate therapy for the satisfied rate zone, as is indicated by the "Treat" symbol 404.

To determine if the ventricular rate is greater than the atrial rate by at least the bias factor, the section 400 of the system 20 determines the sum of a ventricle set of detected ventricular cycle lengths (e.g., last 10) and the sum of an atrial set of detected atrial cycle lengths (e.g., last 10) prior to the end of the duration time interval. The last 10 atrial intervals prior to the end of the duration time interval are assessed after a third fast ventricular interval is detected by the system 20. If fewer than 10 atrial intervals are available, then the intervals available will be used to calculate the average atrial rate. The cycle length sums are converted to ventricular rate averages and atrial rate averages by the section 400. If the ventricular rate average is greater than the atrial rate average by the bias factor then the ventricle is determined to be beating faster than the atrium and therapy is initiated based on the highest satisfied ventricular rate zone. All other detection enhancements that are active are bypassed if the V>A+B detection enhancement is met. If the ventricular rate is not greater, then therapy is inhibited. The value of the bias factor, B, is programmable in the ranges of 5-20 bpm, where 10 bpm is an appropriate number.

Atrial information can also used in the atrial fibrillation detection enhancement 406 for assessing whether the atria are in a state of atrial fibrillation. In fibrillation detection enhancement 406, the system 20 monitors the atrial interval rate and compares it to a preprogrammed atrial fibrillation (AFib) rate threshold value which is used to determine the existence of an atrial fibrillation. Therapy to the ventricles is withheld if the atrial interval rate is above the AFib rate threshold value and the conduction of the ventricular indicates that the underlying cause of a high ventricular rate is due to a ventricular response to fibrillation in the atrium.

The atria are determined to be in fibrillation in the following manner. When the lowest satisfied rate zone's rate duration time interval has expired, a first set of atrial intervals, (e.g., the 10 most recent atrial intervals prior to the expiration of the duration time interval) are examined. Each atrial interval is classified as being either shorter than or longer than the programmed atrial fibrillation rate threshold value AFib. If a predetermined majority number (6 of the last 10 atrial intervals) of the first set of atrial intervals are shorter than the atrial fibrillation interval rate threshold value, the atrial rhythm is declared to be atrial fibrillation. Ventricular stability is then checked (i.e., when the atrial fibrillation detection enhancement is programmed on, the Stability detection enhancement is also activated) and if the system 20 determines that the ventricles are unstable, ventricular therapy will be withheld. In the event that therapy is not delivered, the atrial rate will continue to be examined by the system 20 and as long as a predetermined quorum number (e.g., 4 of 10 subsequent sets of atrial intervals) of subsequent sets of atrial intervals remain shorter than the atrial fibrillation interval rate threshold value, atrial fibrillation is determined to be continuing. Atrial fibrillation rate threshold values can be programmed within the ranges of about 250 to 400 bpm with 250 bpm being a useful value. The atrial fibrillation detection enhancement can also be programmed off.

The Onset rate detection enhancement 408 measures the rate of transition of a ventricular interval rate from a slower sinus rate to tachycardia rate. The Onset rate detection enhancement 408 is intended to enable the system 20 to differentiate physiologic sinus tachycardias, which typically begin slowly and have a gradual onset, from pathological tachycardias, which typically begin in a more abrupt step-like manner. The programmable Onset rate detection enhancement at 408 is limited to the lowest zone of multiple rate zone configuration (e.g., VT for a two rate zone configuration and VT-1 for a three rate zone configuration) and may be used in conjunction with the SRD time-period.

Figure 5:
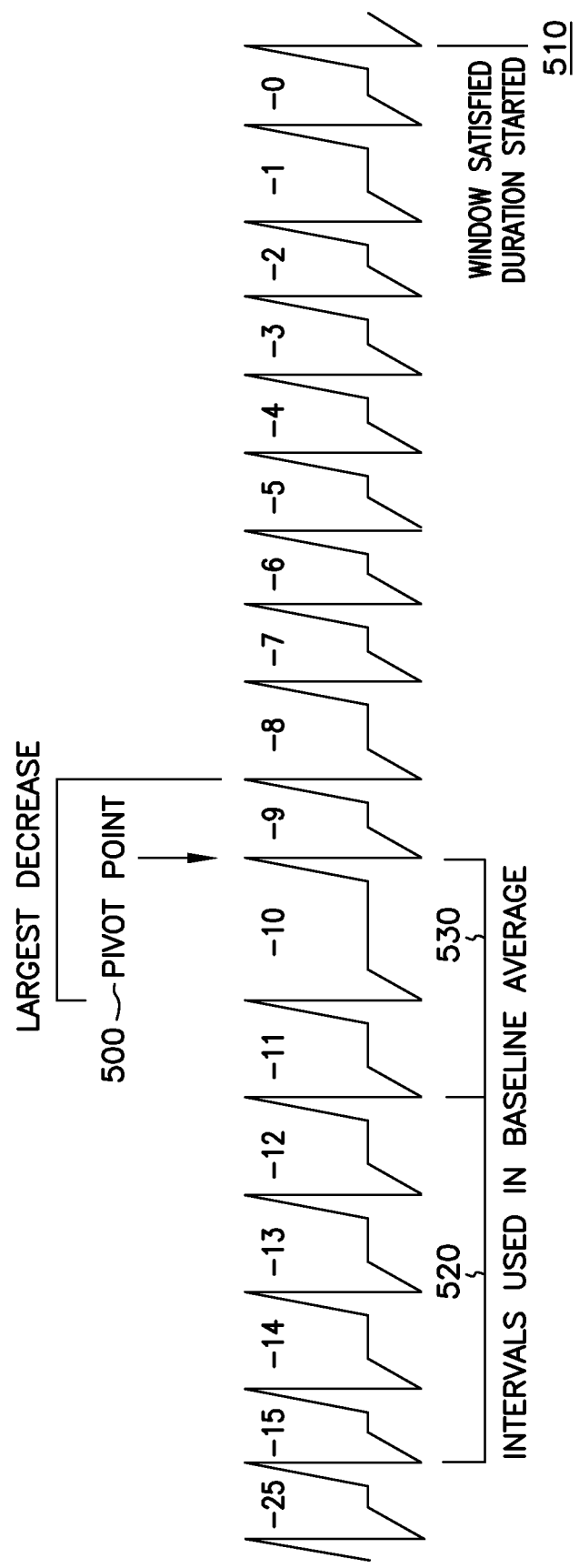
FIG. 5 is a graph illustrating a determination of the presence or absence of sudden onset rate of a ventricular tachycardia by the system according to the present invention.

Referring now to FIG. 5, there is shown a schematic of a series of ventricular intervals used to assess the Onset rate detection enhancement. When a detection window becomes satisfied, the system 20 assesses the Onset rate enhancement by comparing a cycle length change of a pair of adjacent ventricular intervals with a programmed onset rate value in a two step procedure. In the first step, the system 20 locates a pair of adjacent ventricular intervals 500 where the cycle length between the ventricular intervals has decreased the most. This pair of ventricular intervals 500 is called a pivot point, and it is determined using ventricular intervals sensed prior to the start of a cardiac episode 510.

To calculate the pivot point 500, the system 20 begins with the interval that initially satisfied the detection window and started the cardiac episode 510. This interval is called interval −0, and the system 20 scans up to 26 previous ventricular intervals looking for the pivot point. Interval differences are calculated as $(V-V)_{interval(n)} - (V-V)_{interval(N-1)}$; where n=−3 to −25. Pivot point scanning begins at n=−3, because three intervals are required after a potential pivot point interval for the stage two evaluation. Pivot point scanning ends at n=−25 because six intervals are required before the pivot point for the baseline average ventricular rate value calculations.

A programmed onset threshold value is used in assessing the pivot point 500. The system 20 compares the pivot point to the programmed onset threshold value to determine if the pivot point has exceeded the threshold value. If the pivot point decrease has exceeded the programmed threshold value, the system 20 compares the ventricular intervals before and after the pivot point to ensure that the overall ventricular rate has changed by more than the programmed threshold value. The overall ventricular rate change and the programmed threshold value are compared by the system 20 in either absolute time or as a percentage of ventricular interval change. If the pivot point decrease is greater than or equal to the programmed threshold value, then the first stage test result is considered sudden. The programmable ranges for the percentage analysis are between 9 to 50% and for the absolute time analysis are between 50 to 250 milliseconds. The Onset rate enhancement can also be programmed off. The selected Onset rate value represents the minimum difference that must exist between ventricular interval rates that are below the lowest programmed rate threshold and the ventricular intervals that are above the lowest programmed rate threshold.

For a programmed onset threshold in absolute time, the system 20 compares the pivot point decrease to the onset threshold value using absolute time values. If the decrease is greater than the onset threshold value, stage one is satisfied. For threshold as a percentage of interval, the comparison is made using four of six intervals prior to the pivot point to calculate a baseline average ventricular rate value, where the Baseline average=$[(V-V)_{pp(-3)} + (V-V)_{pp(-4)} + (V-V)_{pp(-5)} + (V-V)_{pp(-6)}]/4$, where the values are seen at 520 on FIG. 5. The first two ventricular intervals prior to the pivot point 530 are skipped to avoid counting premature ventricular contractions during a rapid sinus tachycardia. The baseline average is then multiplied by the onset threshold as a percent to convert the threshold into the units of milliseconds (ms). If the pivot point interval decrease is greater than the onset threshold as a percent of interval in ms, then stage one is satisfied, and if not, stage one is not satisfied.

If stage one is satisfied, the system 20 proceeds to stage two. In stage two, the baseline average 520 is compared to the value of the pivot point interval and each of the subsequent three ventricular intervals. If the difference between the baseline average and at least three of the four intervals (i.e., the pivot point interval and the three ventricular intervals) is greater than or equal to the onset threshold value, then the onset is declared sudden. If fewer than three intervals are greater than the onset threshold value, then the onset is declared gradual. This test ensures that the ventricular rate has changed by more than the programmed threshold value over a wider set of ventricular interval samples.

If either stage indicates a gradual onset, therapy will be inhibited in the lowest zone. Therapy will be delivered only if the rate accelerates to a higher zone, the SRD time-period timer expires, or information from the atrial lead determines that the V>A+B detection enhancement has been satisfied.

Referring again to FIG. 4, the Stability detection enhancement 410 is used to distinguish variable ventricular interval rates from stable ventricular interval rates. The system 20 uses the Stability detection enhancement 410 to determine the stability of a ventricular tachyarrhythmia using a weighted average variance of a series of sensed ventricular intervals. This degree of variability, when used by itself, may allow the system 20 to distinguish atrial fibrillation (which may produce greater R-R variability) from monomorphic ventricular tachycardia (MVT) (which is typically stable and pace terminable), and also may help differentiate MVTs from ventricular fibrillation and polymorphic ventricular tachycardias (which are not typically to pace terminable). Based on this differentiation, the system 20 can be programmed to deliver therapy by programming the stability detection enhancement to inhibit delivering therapy at the termination of the duration time interval if the ventricular rate is determined to be unstable. Alternatively, the system 20 can deliver therapy when, at the end of the duration time interval, the ventricular rate is determined to be stable. Assessment of ventricular rate stability begins when the duration time interval starts in a satisfied rate zone.

Figure 6:
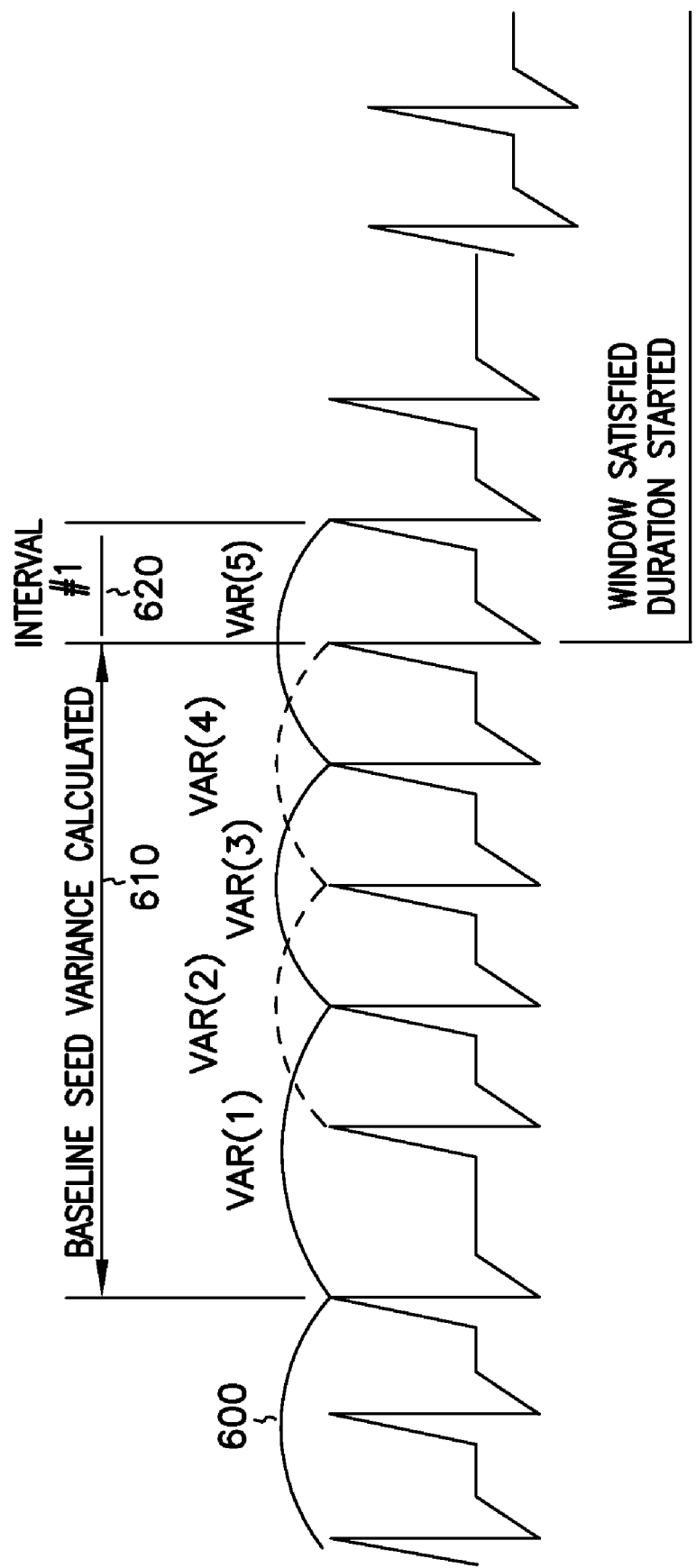
FIG. 6 is a graph illustrating a determination of the stability or instability of a ventricular tachycardia by the system according to the present invention.

Referring now to FIG. 6, the stability detection enhancement uses ventricular interval differences to assess the stability of the ventricular rhythm. Both the ventricular interval differences and an average difference are calculated while the duration time interval is elapsing. The variance from ventricular interval to ventricular interval (VAR(n)) 600 is determined by subtracting each current ventricular interval from the previous ventricular interval using one second as the greatest difference where VAR(n)=absolute value (RR(n−1)−RR(n)). The Stability detection enhancement is "seeded" ($VAR_{SEED}$) by first determining the average variance of the four interval pairs immediately before the start of duration time interval 610, where $VAR_{SEED}=\{VAR(1)+VAR(2)+VAR(3)+VAR(4)\}/4$. For the first ventricular interval 620, the Stability detection enhancement calculates the average variance using the following weighted average formula: $VAR_{AVG}(NEW)=VAR_{SEED}*Kvar+VAR(5)*(1-Kvar)$, where: Kvar=0.875. For each subsequent ventricular interval, starting after the first interval 620, the Stability detection enhancement updates the average variance using the following weighted average formula: $VAR_{avg}(NEW)=VAR_{avg}(NEW-1)*Kvar+VAR(n)*(1-Kvar)$, where: Kvar=0.875 and n=the current interval number. As each new ventricular interval variance is summed into the weighted average, the effect of preceding ventricular intervals on the average variance is diminished. The average variance is updated throughout the cardiac episode. If the average variance is greater that the applicable stability threshold, then the interval is considered unstable.

When the duration time interval is satisfied, the Stability of the ventricular interval is evaluated by comparing the current average variance to a programmed stability threshold value. If the average variance is equal to or greater than the programmed Stability threshold value, the ventricular rate is declared unstable by the system 20. Stability threshold values are programmable within the range about from 6 to 120 ms, where 22 ms is a suitable value. The Stability detection enhancement can also be programmed OFF. The Stability detection enhancement is used in conjunction with the atrial fibrillation detection enhancement when it is enabled in the same zone of a multi-zone configuration.

Referring again to FIG. 4, when the stability detection enhancement is programmed as a therapy inhibitor and an unstable ventricular rhythm is detected, the system 20 inhibits delivering therapy to the heart 30 until the SRD time-period has expired. This is useful for ventricular rhythms originating in the atrium that may appear unstable in the ventricle when the rate exceeds the lowest rate threshold, but the physician does not intend for those rhythms to be treated by the pulse generator. If inhibited, re-evaluation for stability continues on each new detected interval. Evaluation for stability continues for as long as the detection window remains satisfied or until the SRD time has expired (if programmed on). If the ventricular rate becomes stable, treatment is initiated immediately. The enhancement is evaluated for each ventricular interval after the end of duration time interval until the stability enhancement is no longer met (i.e., the ventricular rate becomes stable) or the SRD time-period timer expires. Programming the stability detection enhancement to inhibit delivering therapy if the ventricular rate is unstable is limited to the lowest zone of a two- or three-zone configuration. The Stability detection enhancement set to inhibit may also be used in conjunction with the SRD time-period.

Alternatively, the Stability detection enhancement can be programmed to deliver the first shock therapy if the ventricular rhythm determined to be unstable. When the system 20 is programmed to deliver shock therapy if the ventricular rhythm is unstable, the Stability detection enhancement determines if the remaining ATP therapy should be skipped over in preference of the first programmed shock therapy (which may be low or high energy) for the satisfied rate zone. Dynamic ventricular arrhythmias such as polymorphic VT or VF (that generally respond best to shock therapy) may be sensed at a rate lower than the highest rate threshold and may be sensed as unstable. Since the sensed rhythm may be detected in a lower zone in which ATP may be programmed, the Stability parameter may be used to skip over the programmed ATP therapies and instead provide shocks to the patient. Stability is evaluated on each detected ventricular cycle, including evaluation between pacing bursts of an ATP scheme. Once a shock has been delivered in an episode, this Stability function (programmed to shock if unstable) no longer affects therapy selection. The Stability detection enhancement programmed in this manner can be used in the VT zone of a two-zone configuration or three zone configuration. It cannot be programmed in this manner in a two zone configuration if the Stability detection enhancement is already programmed to inhibit delivering therapy if the ventricular rate is unstable or if the Onset rate detection enhancement is programmed on.

Referring to FIG. 4, the Onset rate and Stability detection enhancements programmed as inhibitors may be combined to provide greater specificity in characterizing ventricular tachycardias which should not be treated by the system 20. The two detection enhancements can be programmed such that to initiate therapy, Onset rate AND Stability must be satisfied 450, or such that either Onset rate or Stability must be satisfied 460. If the combination programmed is Onset rate OR Stability, therapy is initiated immediately at the end of duration if either parameter is satisfied; that is, the rhythm is sudden or stable (the OR condition is satisfied). If the combination programmed is Onset rate AND Stability, therapy is initiated only if parameters are satisfied; that is, the rhythm is sudden and stable (the AND condition is satisfied). When these two combinations (AND/OR) are used in conjunction with the SRD time-period, and the and/or conditions are not satisfied, therapy will be inhibited until the SRD time-period times out. The Onset rate and Stability inhibitors is limited to the lowest zone of a multiple rate zone configuration.

If AFib rate threshold/AFib stability and Onset rate are both programmed on, the combination is an AND condition. This is, to initiate therapy the rhythm must have a sudden Onset rate and either the ventricular rate must be stable or the atrial rate must be less than the AFib rate threshold.

Monomorphic VT is an arrhythmia which is likely to be pace terminable, and it is sensed as highly stable from beat to beat. In contrast, AF, polymorphic VT, and VF are characterized by erratic or unstable sensed rates in the ventricle, and are not generally pace terminable using ventricular pacing. When selected by the user and an unstable rhythm is declared, any programmed anti-tachycardia pacing therapies is bypassed in order to deliver shock therapy. Once a shock has been delivered in an episode the stability as an accelerator function no longer affect therapy selection. Stability as an accelerator is evaluated only once at the expiration of the duration time interval and is used in the VT rate zone of a multi-zone configuration.

Figure 7:
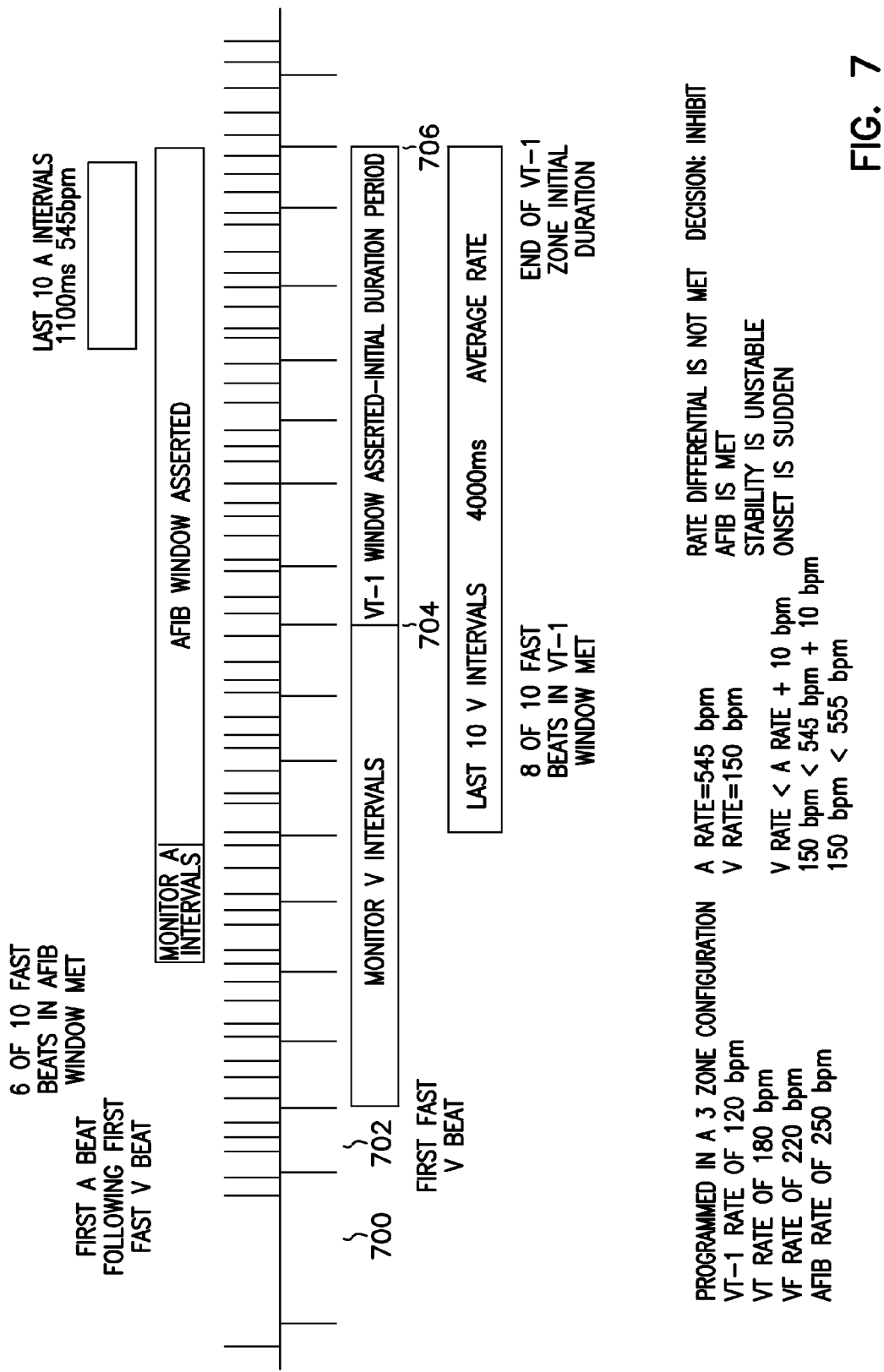
FIG. 7 is a chart illustrating an example of the use of the detection enhancements.

Referring now to FIG. 7, there is shown an example of the use of the detection enhancements according to the present invention. The system 20 is initially programmed with a three zone configuration, where the VF, VT, and VT-1 rate zones are enabled. The lower rate threshold for the VF rate zone is programmed to 250 bpm, for the VT rate zone it is programmed to 180, and for the VT-1 rate zone it is programmed to 120 bpm. The programmed atrial fibrillation rate threshold value is programmed to 250 bpm.

The systems 20 is programmed to detect ventricular intervals in a shifting series of 10 of the most recent consecutive ventricular R-waves. As previously discussed this shifting sampling of ventricular intervals is called a detection window. The system 20 assess the sensed ventricular interval in relation to each of the rate zones, where as each new ventricular interval rate is measured by the system 20 it is compared to each rate zone's lower rate threshold. The ventricular interval rates are classified as being either a fast or a slow ventricular interval with respect to each of the rate zones. For this example, the predetermined percentage of fast ventricular interval rates within a detection window necessary to satisfy a rate zone detection window is programmed to eighty percent, or 8 of the 10 most recent consecutive ventricular R-waves.

By way of this example, it is assumed that the patient's ventricular rate has increased from 85 bpm to 150 bpm between a first ventricular interval 700 and a second ventricular interval 702. The system 20 continues to monitor and classify each detected ventricular interval as either fast or slow with respect to each programmed rate zone. The system 20 becomes "satisfied" that the ventricular rate intervals for the heart are properly classified in the VT-1 rate zone at 704, as 6 of 10 fast ventricular beats have fallen within the VT-1 rate zone. The system 20 then begins the duration time interval and continues to monitor the ventricular interval rates within the shifting detection window to be sure that the ventricular rate interval for the heart remains properly classified in the VT-1 rate zone. The maintenance percentage for the ventricular interval rates in the subsequent detection windows is programmed to be 60 percent, or 6 of the 10 most recent consecutive ventricular R-waves.

The duration time interval for the VF rate zone is programmed to 1 seconds, for the VT rate zone it is programmed to 1 seconds, and for the VT-1 rate zone it is programmed to 2.5 seconds. FIG. 7 shows a selected region of sensed ventricular and atrial intervals surrounding the ventricular interval which causes the VT-1 rate zone to become satisfied at 704, and it is assumed for this example that the VT-1 rate zone detection window remains satisfied throughout the duration of it's duration time interval time, and the higher rate zones (i.e., the VT and VF rate zones) do not become satisfied.

The ventricular tachycardia therapy for the VT-1 rate zone is programmed to first deliver an ATP burst therapy then proceed to a ATP ramp therapy for its ATP therapy prescriptions. Five cardioverting/defibrillation shocks are programmable into the system 20 for the VT-1 rate zone, where the first cardioverting or defibrillation shock is programmed at 5 joules and the second cardioverting or defibrillation shock is programmed at 10 joules. As previously mentioned, the last three potential cardioverting/defibrillation shocks are given at the maximum shock output of 29 joules.

Once the detection window contains three fast consecutive ventricular beats, the system begins to monitor the atrial intervals and begins to analyze the programmed detection enhancements. All four detection enhancements (V>A+B, atrial fibrillation detection, Onset rate, and Stability) and the SRD time-period are programmed on, with the Stability and the atrial fibrillation detection enhancements being programmed as a therapy inhibitor. The bias factor, B, is programmed with a value of 10 bpm and the SRD time-period is programmed with a duration value of 5 minutes. As previously discussed, if a detection enhancement as an inhibitor (i.e., the Stability detection enhancement for the VT-1 rate zone) is inhibiting therapy and the detection window is remaining satisfied for the VT-1 rate zone, the SRD time-period begins at the end of the VT-1 rate zone duration time interval. If the detection window continues to remain satisfied during the SRD time-period, the programmed therapy will be delivered at the end of the SRD time-period.

Referring again to FIG. 7, upon determining that the heart has satisfied the duration time interval for the VT-1 rate zone at 706, the system 20 simultaneously analyzes all four programmed detection enhancements. The system 20 has detected and analyzed the atrial rate to be 545 bpm and the ventricular rate to be 150 bpm. The V>A+B detection enhancement is, therefore, not satisfied and therapy with respect to the V>A+B detection enhancement is inhibited. Concurrent with this assessment, the system 20 also utilizes the Onset rate detection enhancement to calculate a pivot point as previously discussed. By way of this example it is assumed that the system determines that the pivot point decrease is sudden according to the procedure described above, therefore, stage one of the Onset rate detection enhancement is satisfied. During the second stage of the Onset rate assessment, the baseline average value is compared to the value of the pivot point interval and each of the subsequent three ventricular intervals, where, for the example, the system 20 determines that the difference between the baseline average and the pivot point interval and the three ventricular intervals is greater than or equal to the onset threshold value. The onset is, therefore, determined to be sudden.

The ventricular stability is also assessed concurrently with the V>A+B and Onset rate detection enhancements by the Stability detection enhancement. Stability is assessed as previously discussed and the system 20 determines that the ventricular rate is unstable. Once the VT-1 duration time interval has expired, the system 20 examines and classifies the 10 most recent atrial intervals as being either shorter or longer than the programmed atrial fibrillation rate threshold value. If a majority number of the first set of atrial intervals (6 of the last 10 atrial intervals) are classified as being shorter than the atrial fibrillation rate threshold value AFib, the atrial rhythm is declared to be atrial fibrillation. FIG. 7 indicates that the 10 most recent atrial intervals after the VT-1 duration time interval expired occurred over a 1100 millisecond interval, which is a atrial rate of 545 bpm indicating the presence of an atrial fibrillation. As a result of the atria being in a state of fibrillation and the ventricular interval rate being determined to be both sudden and unstable, the system 20 inhibits delivering therapy at the expiration of the VT-1 rate zone duration time interval until either the SRD time-period has expired, until the ventricular interval rate becomes stable, or until the atrial fibrillation criterion are no longer satisfied. Alternatively, if the rate accelerates to a higher rate zone and the duration time interval for the higher rate zone is satisfied, therapy is initiated without waiting for SRD time period to time out.

What is claimed:

1. A method, comprising:
   sensing atrial events and ventricular events;
   determining ventricular interval rates from pairs of consecutively sensed ventricular events in a detection window;
   classifying each ventricular interval rate of the ventricular interval rates as a fast ventricular interval or a slow ventricular interval for a rate zone by comparing the each ventricular interval rate to a lower rate threshold of the rate zone;
   declaring the detection window satisfied in response to a first predetermined percentage of the ventricular interval rates in the detection window being classified as the fast ventricular intervals;
   starting a first time interval in response to the detection window being declared satisfied, the first time interval having a duration for the rate zone; and
   determining whether to inhibit a ventricular tachycardia therapy at the end of the first time interval.

2. The method of claim 1, wherein determining whether to inhibit the ventricular tachycardia therapy comprises determining whether the fast ventricular intervals sustain during the first time interval.

3. The method of claim 2, wherein determining whether the fast ventricular intervals sustain comprises:
   declaring that the detection window remains satisfied in response to a second predetermined percentage of the ventricular interval rates in the detection window being classified as the fast ventricular intervals; and
   resetting the first time interval to zero in response to the detection window failing to remain satisfied during the first time interval.

4. The method of claim 2, wherein determining whether to inhibit the ventricular tachycardia therapy comprises determining an origin of the fast ventricular intervals during the first time interval.

5. The method of claim 4, wherein determining whether to inhibit the ventricular tachycardia therapy comprises:
   determining an average atrial rate from the sensed atrial events during the first time interval;
   determining an average ventricular rate from the sensed ventricular events during the first time interval; and
   inhibiting the ventricular tachycardia therapy at the end of the first time interval in response to the average ventricular rate not being greater than the average atrial rate by at least a bias factor during the first time interval.

6. The method of claim 4, wherein determining whether to inhibit the ventricular tachycardia therapy comprises:
   determining a ventricular rate from the sensed ventricular events during the first time interval;
   determining whether an onset rate is gradual during the first time interval, wherein the onset rate is the rate of transition of the ventricular rate from a slower sinus rate to a tachycardia rate, and the onset rate is gradual when the onset rate is equal to or greater than an onset threshold value; and
   inhibiting the ventricular tachycardia therapy at the end of the first time interval in response to the onset rate being gradual during the first time interval.

7. The method of claim 4, wherein determining whether to inhibit the ventricular tachycardia therapy comprises:
   determining a ventricular rate from the sensed ventricular events during the first time interval; and
   determining whether the ventricular rate is unstable during the first time interval, wherein the ventricular rate is unstable when an average variance of ventricular intervals exceeds a stability interval threshold value; and
   inhibiting the ventricular tachycardia therapy at the end of the first time interval in response to the ventricular rate being unstable during the first time interval.

8. The method of claim 7, wherein determining whether to inhibit the ventricular tachycardia therapy further comprises:
   determining an occurrence of atrial fibrillation using the sensed atrial events during the first time interval; and
   inhibiting the ventricular tachycardia therapy at the end of the first time interval in response to the ventricular rate being unstable and atrial fibrillation being occurring during the first time interval.

9. A system, comprising:
   sensing circuitry configured to sense atrial events and ventricular events;
   therapy delivery circuitry configured to deliver a ventricular tachycardia therapy; and
   control circuitry configured to:
   determine ventricular interval rates from pairs of consecutively sensed ventricular events in a detection window:
   classify each ventricular interval rate of the ventricular interval rates as a fast ventricular interval or a slow ventricular interval for a rate zone by comparing the each ventricular interval rate to a lower rate threshold of the rate zone;
   declare the detection window satisfied in response to a first predetermined percentage of the ventricular interval rates in the detection window being classified as the fast ventricular intervals;
   start a first time interval having a duration for the rate zone in response to the detection window being declared satisfied; and
   determine whether to inhibit a ventricular tachycardia therapy at the end of the first time interval.

10. The system of claim 9, wherein the control circuitry is further configured to:
    determine whether the fast ventricular intervals sustain during the first time interval;

declare that the detection window remains satisfied in response to a second predetermined percentage of the ventricular interval rates in the detection window being classified as the fast ventricular intervals; and reset the first time interval to zero in response to the detection window failing to remain satisfied during the first time interval.

11. The system of claim 9, wherein the control circuitry is further configured to:

detect ventricular tachycardia and ventricular fibrillation during the first time interval; and reset the first time interval in response to a detection of the ventricular tachycardia or the ventricular fibrillation during the first time interval.

12. The system of claim 9, wherein the control circuitry is further configured to determine an origin of the fast ventricular intervals during the first time interval.

13. The system of claim 12, wherein the control circuitry is further configured to:

determine an average atrial rate from the sensed atrial events during the first time interval;

determine an average ventricular rate from the sensed ventricular events during the first time interval;

determine whether the average ventricular rate is not greater than the average atrial rate by a east a bias factor during the first time interval; and inhibit the ventricular tachycardia therapy at the end of the first time interval in response to the average ventricular rate not being greater than the average atrial rate by at least the bias factor during the first time interval.

14. The system of claim 12, wherein the control circuitry is further configured to:

determine a ventricular rate from the sensed ventricular events during the first time interval;

determine whether an onset rate is gradual during the first time interval, wherein the onset rate is the rate of transition of the ventricular rate from a slower sinus rate to a tachycardia rate, and the onset rate is gradual when the onset rate is equal to or greater than an onset threshold value; and inhibit the ventricular tachycardia therapy at the end of the first time interval in response to the onset rate being gradual during the first time interval.

15. The system of claim 12, wherein the control circuitry is further configured to:

determine a ventricular rate from the sensed ventricular events during the first time interval;

determine whether the ventricular rate is unstable during the first time interval, wherein the ventricular rate is unstable when an average variance of ventricular intervals exceeds a stability interval threshold value; and inhibit the ventricular tachycardia therapy at the end of the first time interval in response to the ventricular rate being unstable during the first time interval.

16. The system of claim 15, wherein the control circuitry is further configured to:

determine an occurrence of atrial fibrillation from the sensed atrial events during the first time interval; and inhibit the ventricular tachycardia therapy at the end of the first time interval in response to the ventricular rate being unstable and atrial fibrillation being during the first time interval.

17. A system, comprising:

means for sensing atrial events and ventricular events:

means for determining ventricular interval rates from pairs of consecutively sensed ventricular events in a detection window;

means for classifying each ventricular interval rate of the ventricular interval rates as a fast ventricular interval or a slow ventricular interval for a rate zone by comparing each ventricular interval rate to a lower rate threshold of the rate zone;

means for declaring the detection window satisfied when a first predetermined percentage of the ventricular interval rates in the detection window are classified as the fast ventricular intervals;

means for starting a first time interval once the detection window is declared satisfied, the first time interval having a duration for the rate zone; and means for determining whether to inhibit a ventricular tachycardia therapy at the end of the first time interval.

18. The system of claim 17, wherein the means for determining whether to inhibit the ventricular tachycardia therapy comprises means for determining whether the fast ventricular intervals sustain during the first time interval.

19. The system of claim 18, wherein the means for determining whether the fast ventricular intervals sustain comprises:

means for declaring that the detection window remains satisfied when a second predetermined percentage of the ventricular interval rates in the detection window are classified as the fast ventricular intervals; and means for resetting the first time interval to zero when the detection window fails to remain satisfied during the first time interval.

20. The system of claim 18, wherein the means for determining whether to inhibit the ventricular tachycardia therapy comprises means for determining an origin of the fast ventricular intervals during the first time interval.

* * * * *